US011856945B2

(12) United States Patent
Singamaneni et al.

(10) Patent No.: US 11,856,945 B2
(45) Date of Patent: Jan. 2, 2024

(54) METHODS AND SYSTEMS FOR PREPARING AND PRESERVING A BIOLOGICAL SAMPLE

(71) Applicants: Srikanth Singamaneni, St. Louis, MO (US); Congzhou Wang, St. Louis, MO (US); Jeremiah J. Morrissey, St. Louis, MO (US); Evan D. Kharasch, St. Louis, MO (US)

(72) Inventors: Srikanth Singamaneni, St. Louis, MO (US); Congzhou Wang, St. Louis, MO (US); Jeremiah J. Morrissey, St. Louis, MO (US); Evan D. Kharasch, St. Louis, MO (US)

(73) Assignee: Washington University, St. Louis, MO (US)

( * ) Notice: Subject to any disclaimer, the term of this patent is extended or adjusted under 35 U.S.C. 154(b) by 724 days.

(21) Appl. No.: 16/606,482

(22) PCT Filed: Apr. 20, 2018

(86) PCT No.: PCT/US2018/028591
§ 371 (c)(1),
(2) Date: Oct. 18, 2019

(87) PCT Pub. No.: WO2018/195438
PCT Pub. Date: Oct. 25, 2018

(65) Prior Publication Data
US 2020/0305416 A1 Oct. 1, 2020

Related U.S. Application Data

(60) Provisional application No. 62/488,231, filed on Apr. 21, 2017.

(51) Int. Cl.
*G01N 33/68* (2006.01)
*G01N 21/33* (2006.01)
(Continued)

(52) U.S. Cl.
CPC ......... *A01N 1/0231* (2013.01); *G01N 1/4044* (2013.01)

(58) Field of Classification Search
CPC ...... A01N 1/0231; G01N 1/4044; G01N 1/36; C12N 15/10
See application file for complete search history.

(56) References Cited

U.S. PATENT DOCUMENTS

| 2013/0274087 A1* | 10/2013 | da Silva Pinto | ..... B01J 20/3217 502/4 |
| 2016/0101192 A1* | 4/2016 | Berthelot | ............. A61K 8/8152 526/170 |

(Continued)

FOREIGN PATENT DOCUMENTS

WO    WO-2017223046 A1 * 12/2017

OTHER PUBLICATIONS

Liang, Kang, et al. "Biomimetic mineralization of metal-organic frameworks as protective coatings for biomacromolecules." Nature communications 6.1 (2015): 1-8. (Year: 2015).*

(Continued)

*Primary Examiner* — Jennifer Wecker
*Assistant Examiner* — Oyeleye Alexander Alabi
(74) *Attorney, Agent, or Firm* — Armstrong Teasdale LLP

(57) ABSTRACT

Methods and systems for preparing and preserving biological samples are disclosed herein. A method comprises contacting a preserving agent with a biological sample to form a mixture, wherein the preserving agent is selected from at least one of a metal-organic framework (MOF) encapsulant or a precursor forming a MOF encapsulant, and wherein the biological sample comprises at least one target analyte. A system comprises a preserving agent selected from at least one of a metal-organic framework (MOF) encapsulant or a precursor forming a MOF encapsulant; and a substrate (Continued)

configured to receive a drop cast mixture of the preserving agent and a biological sample, wherein the biological sample comprises at least one target analyte.

10 Claims, 34 Drawing Sheets

(51) Int. Cl.
| | |
|---|---|
| *G01N 21/64* | (2006.01) |
| *G01N 33/52* | (2006.01) |
| *C07C 309/05* | (2006.01) |
| *C07C 309/73* | (2006.01) |
| *A01N 1/02* | (2006.01) |
| *G01N 1/40* | (2006.01) |

(56) References Cited

U.S. PATENT DOCUMENTS

2016/0231233 A1  8/2016  Wang et al.
2021/0284951 A1* 9/2021  Klapproth .............. G01N 1/286

OTHER PUBLICATIONS

"Human serum albumin: from bench to bedside." Molecular aspects of medicine 33.3 (2012): 209-290 (Year: 2012).*
Billett, Henny H. "Hemoglobin and hematocrit." Clinical Methods: The History, Physical, and Laboratory Examinations. 3rd edition (1990). https://www.ncbi.nlm.nih.gov/books/NBK259/ (Year: 1990).*
International Search Report for International Patent Application No. PCT/US2018/028591, dated Oct. 25, 2018, 2 pages.
Eslamian et al., "Ultrasonic Substrate Vibration-Assisted Drop Casting (SVADC) for the Fabrication of Photovoltaic Solar Cell Arrays and Thin-Film Devices", Nanoscale Research Letters, 2015, 5 pages, vol. 10, No. 462.
Iang et al., "Biomimetic mineralization of metal-organic frameworks as protective coatings for biomacromolecules", Nature Communications, 2015, 8 pages, vol. 6, No. 7240.
Wang et al., "Metal-Organic Framework as a Protective Coating for Biodiagnostic Chips", Advanced Materials, 2017, 14 pages, vol. 29, No. 7.
Wang et al., "Metal-Organic Framework Encapsulation for Biospecimen Preservation", Chemistry of Materials, 2018, pp. 1291-1300, vol. 30, No. 4.

* cited by examiner

METHODS AND SYSTEMS FOR PREPARING AND PRESERVING A BIOLOGICAL SAMPLE

CROSS-REFERENCE TO RELATED APPLICATION

This application is a US National Stage Entry of International Patent Application No. PCT/US2018/028591, filed Apr. 20, 2018, which claims the benefit of priority to U.S. Provisional Application Ser. No. 62/488,231, filed on Apr. 21, 2017, entitled METHOD FOR PRESERVING A BIOLOGICAL SAMPLE, the entire contents of which are incorporated herein by reference in their entireties.

ACKNOWLEDGEMENT OF GOVERNMENT SUPPORT

This invention was made with government support under CA141521, DK100759 from the National Institutes of Health; and FA9550-15-1-0228 awarded by the Air Force Office of Scientific Research. The government has certain rights in the invention.

FIELD

The present disclosure generally relates to methods and systems for preparing and preserving a biological sample.

BACKGROUND

The availability of high-quality biospecimens such as blood and urine is critical to biomedical research and clinical diagnosis. Unfortunately, due to the poor stability of molecular biomarkers (especially proteins) in these biofluids at ambient and elevated temperatures, they are prone to lose their structure and biofunctionality during the pre-analytical stage (i.e., the preparation, storage or transportation period between sample collection and analysis). For instance, when refrigeration is not maintained, blood-derived biospecimens degrade quickly, accounting for up to 67% of all laboratory testing errors. This requires investigators and clinicians to dedicate a significant fraction of budget to refrigeration or "cold chain" costs associated with biospecimen storage or transportation. More importantly, the refrigeration and "cold chain" are simply not feasible in resource-limited settings (e.g., low and middle income countries), which hinders biospecimen procurement, disease screening, early diagnosis and therapeutic intervention in underserved populations since it is impractical, if not impossible, to expect patients scattered in rural areas to travel and access an extremely limited number of hospitals and clinical laboratories for screening and diagnosis. A feasible solution to the aforementioned challenges is a refrigeration-free biospecimen preservation technology that can be implemented in resource-limited settings (e.g., absence of electricity, refrigeration, trained personnel) and underserved populations to efficiently collect, process and ship well-preserved biospecimens to centralized clinical/research laboratories and hospitals with qualified facilities for analysis.

Considering that the Clinical and Laboratory Standards Institute (CLSI) recommends urinalysis and culture and testing within 2 hours of urine sample collection, urinary samples are often treated with preservatives such as boric acid, tartaric acid, and chlorhexidine to extend the sample storage time if analysis within two hours of sample collection is not feasible. However, these preservatives are applicable only for short preservation times ranging from 24-72 hours, which are not sufficient for implementation in resource-limited settings where the time lapse between sample collection and analysis can be much longer. Moreover, the preservation timescales with the existing preservatives are also not sufficient for research biospecimens used for biomarker discovery and validation, which often involves months to years. Other approaches to dry blood samples, such as isothermal vitrification, lyophilization or within a solid matrix such as silk fibroin, have been reported. In the isothermal vitrification and lyophilization approaches, sugars such as sucrose and trehalose are often added into protein solution in order to form a sugar-glass matrix for stabilizing proteins. However, vitrification and lyophilization of protein with sugars are difficult to implement in resource-limited settings and in some cases lack of control of sugar crystallization can lead to protein aggregation. Drying blood in a silk fibroin matrix represents a novel approach for long-term biofluid preservation without refrigeration. However, the technology involves the use of silk fibroin solution with limited temperature and environmental stability and relatively short shelf-life, making it difficult to implement in resource-limited settings.

Since the 1960s, dried blood spots (DBS), a paper card system, has been used to capture blood components onto an absorbent filter paper matrix as the water phase evaporates. This method is highly convenient since the drying process decreases sample weight by over 90%, thus alleviating transport burden, improving the biospecimen collection and handling capability in resource-limited settings, and allowing on-demand sample restoration and analysis. This method has not been widely implemented for biofluid sample collection and storage so far because of the following two reasons: i) inaccuracy in determining original protein biomarker concentration in biofluids; the sample restoration in this approach involves elusion from a small portion of the dried spot (using a punch) and the original protein biomarker concentration in biofluids is estimated from the ratio of punched area to the entire blood spot area. Considering the uncertain initial sample volume and inhomogeneous distribution of the dried proteins on the paper surface, this concentration estimation method is not accurate and thus the DBS method, so far, is mainly used as a semi-quantitative approach for neonatal screening; and, ii) refrigeration is still required for storage since analytes on DBS stored in harsh environments (e.g., elevated temperatures) can quickly degrade. It is also reported that the addition of zinc ions (such as zinc sulfate) can enhance the stability of specific types of proteins. However, none of the existing methods can be considered a "universal biospecimen preservation technique," which would allow both long-term storage without refrigeration and implementation in resource-limited settings.

Further, therapeutic proteins have gained extensive attention in the pharmaceutical industry owing to their high specificity and therapeutic effectiveness, as well as applications in a broad range of diseases such as cancers, metabolic disorders, autoimmune diseases, chronic inflammatory diseases, cardiovascular diseases and infectious diseases. Unfortunately, due to the structural flexibility and susceptibility to environmental stressors, the increasing use of therapeutic proteins also poses an important challenge related to their instability, which not only leads to decreased bioactivity, but may also potentially elicit undesired immunological responses. At present, lyophilization or freeze-drying is the most widely used approach to stabilize these proteins, although elevated temperature and moisture (even trace amount) still need to be avoided during protein storage in dry state. Apart from solid forms, a large portion of therapeutic proteins today are formulated as aqueous solutions in a ready-to-use form, especially for patients in resource-limited settings and requiring rapid administration. These formulations must be stored at low temperature, which typically extends their shelf-life, but at the cost of an extensive distribution network of refrigeration—the "cold chain"—to maintain an optimal temperature during transport, storage, and handling.

Two alternative approaches to increase protein stability are mutagenesis and chemical modification via modifying the intrinsic structure of proteins. However, in addition to the complex procedure, care must be taken not to compromise protein bioactivity. Another approach to improve the stability is to add sugars into protein solutions, whereas this method still requires refrigeration or freeze-drying and in some cases the lack of control of sugar crystallization can lead to protein aggregation. Because of prevalent public health challenges, natural disasters, and rising global demand for protein therapeutics, the shortcomings of current preservation approaches create an urgent need for a universal stabilization and preservation strategy for therapeutic proteins in solution against various stressors, preferably, without the refrigeration requirement and protein modification.

BRIEF DESCRIPTION OF THE DISCLOSURE

In one embodiment of the present disclosure, a method of preparing a biological sample is provided. The method comprises contacting a preserving agent with a biological sample to form a mixture. The preserving agent is selected from at least one of a metal-organic framework (MOF) encapsulant or a precursor forming a MOF encapsulant. The biological sample comprises at least one target analyte.

In another aspect, a system for preparing a biological sample is provided. The system comprises a preserving agent selected from at least one of a metal-organic framework (MOF) encapsulant or a precursor forming a MOF encapsulant. The system further comprises a substrate configured to receive a drop cast mixture of the preserving agent and a biological sample. The biological sample comprises at least one target analyte.

BRIEF DESCRIPTION OF THE DRAWINGS

Aspects will be readily understood by the following detailed description in conjunction with the accompanying drawings. Aspects are illustrated by way of example and not by way of limitation in the figures of the accompanying drawings.

DETAILED DESCRIPTION

Figure 1:
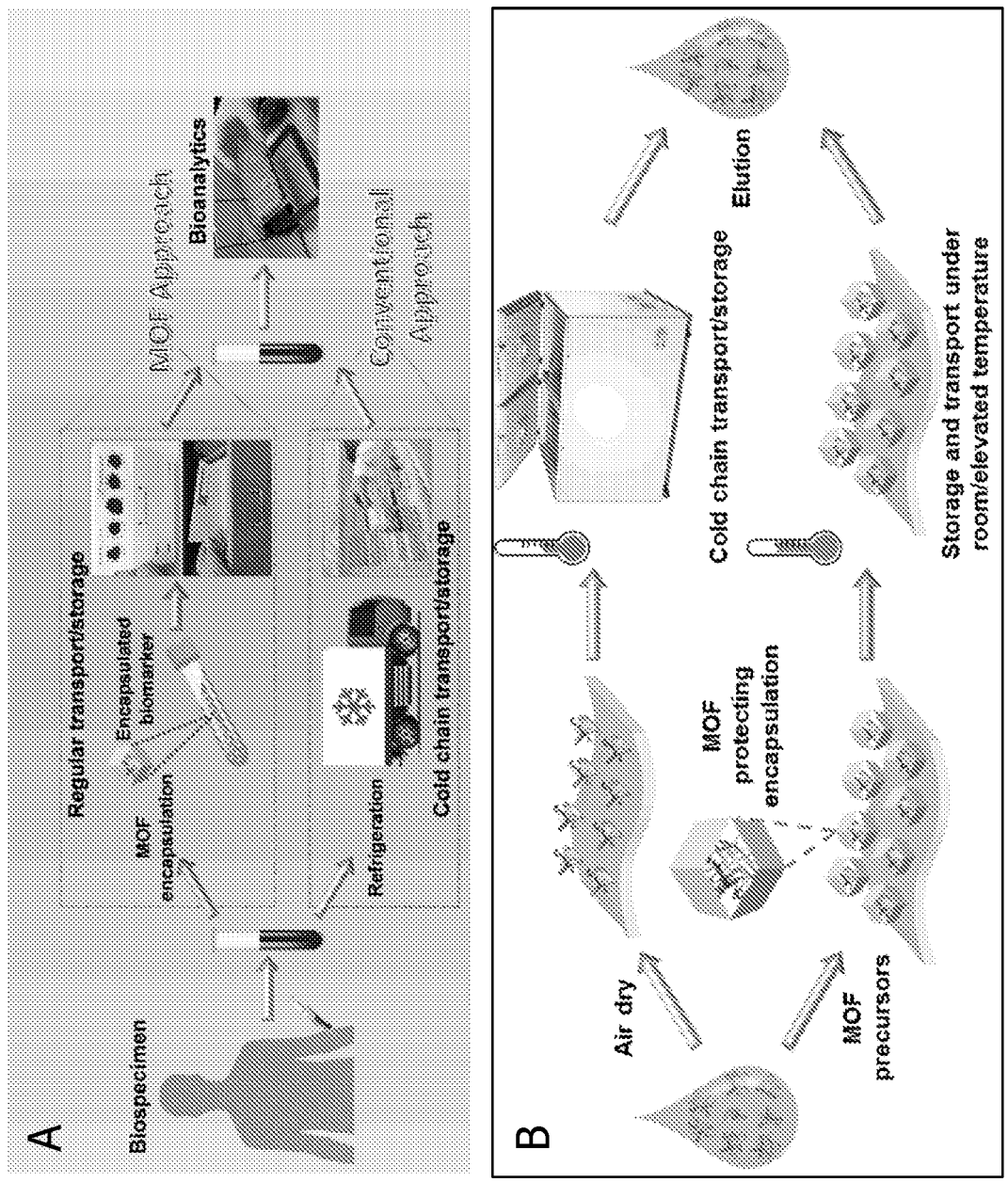
FIG. 1A depicts an exemplary embodiment of a schematic illustration of the concept of using MOF encapsulation for biospecimen preservation in accordance with the present disclosure.
FIG. 1B depicts another exemplary embodiment of a schematic illustration of the concept of using MOF encapsulation for biospecimen preservation in accordance with the present disclosure.

The present disclosure describes using metal-organic frameworks as a protective encapsulant for biospecimen preparation and preservation.

Handling, transport and storage of biospecimens such as blood and urine without refrigeration are extremely challenging. This formidable challenge leads to an inevitable reliance on a "cold chain" for shipping, handling and storage of biospecimens throughout the world. The cold chain requirement precludes biospecimen procurement from underserved populations and resource-limited settings where refrigeration and electricity are not reliable or even available. A universal biospecimen preservation approach is described herein based on nanoporous metal-organic framework (MOF) material encapsulation for preserving protein biomarkers in biofluids under normal (non-refrigerated) storage conditions. Using urinary NGAL and serum/plasma CA-125 as the model protein biomarkers, nanoporous MOF material (e.g., zeolitic imidazolate framework-8 (ZIF-8)) encapsulation preserves protein biomarkers in urine, serum, plasma and blood at room temperature and 40° C., with comparable preservation efficacy to the refrigeration method (freezing liquid samples at −20° C.). The protein biomarkers in the relevant biofluids are first encapsulated within the nanoporous crystals (i.e., ZIF-8) and then dried on paper substrates via a dry spot sample collection method, greatly improving biospecimen collection and handling capability in resource-limited settings. Overall, this energy-efficient and environmentally-friendly approach will not only alleviate the huge financial and environmental burdens associated with "cold chain" facilities but will also extend biomedical research benefits to underserved populations by acquiring reliable clinical samples from regions/populations currently inaccessible.

In some embodiments, a facile approach is described using a MOF encapsulant (e.g., ZIF-8) for preserving protein therapeutics, which are prone to lose their structure and bioactivity under various environmental stressors. In some embodiments, the prototypic protein therapeutic, insulin, is encapsulated and preserved against different harsh conditions that may be encountered during storage, formulation and transport, including elevated temperatures, mechanical agitation and organic solvent. Both immunoassay and spectroscopy analysis demonstrate the preserved chemical stability and structural integrity of insulin offered by the ZIF-8 encapsulation. Biological activity of ZIF-8 preserved insulin after storage under accelerated degradation conditions (i.e. 40° C.) was evaluated in vivo using a diabetic mouse model, and showed comparable bioactivity to refrigeration-stored insulin (−20° C.). ZIF-8 preserved insulin had low cytotoxicity in vitro and did not cause side effects in vivo. Furthermore, in some embodiments, ZIF-8 residue is completely removed by a purification step before insulin administration. This biopreservation approach is potentially applicable to diverse protein therapeutics, thus extending the benefits of advanced biologics to resource-limited settings and underserved populations/regions.

In some embodiments, insulin is selected as a model therapeutic protein because of its extensive clinical usage and well-established structure and bioactivity assays. The required storage for insulin is 2-8° C. since it exhibits a 10-fold or more increase in degradation rate for each 10° C. increment in temperature above 25° C. This requirement impedes the use of temperature-sensitive insulin in pre-hospital and resource-limited settings such as disaster-struck regions and rural clinics in developing countries with low and moderate incomes, where refrigeration and electricity are not reliable or even not available. Insulin is also prone to denaturation and irreversible aggregation when subjected to organic solvents and mechanical agitation, which could be encountered during formulation of nano/microparticle delivery systems and transport. As with most proteins, previous stabilization methods mainly focused on mutagenesis and chemical modification of insulin. Mutagenesis can produce ultra-stable insulin analog but this requires a priori knowledge of possible degradation pathways and may not be applicable to other proteins since in some cases modification of even a single amino acid may disrupt the tertiary structure of a protein. Conjugation of insulin with glycopolymers containing trehalose side chains can enhance both insulin stability and pharmacokinetics, while the activity of the insulin is compromised due to the steric hindrance of insulin-polymer conjugates binding to the receptor. As described herein, ZIF-8 (representative MOF) encapsulation preserves insulin (representative protein therapeutic) structure and activity against various environmental stressors during formulation, transport and storage. In some embodiments, ZIF-8 encapsulation preserves insulin against elevated temperatures, organic solvent and mechanical agitation. ZIF-8 preserved insulin is also evaluated in vivo, and shown to retain bioactivity. The ZIF-8 encapsulation approach does not require any modification to the insulin structure and in some embodiments the ZIF-8 residue is completely removed by a purification step before insulin administration. The ensuing rapid release of encapsulated insulin within a minute enables on-demand reconstitution and usage, thus extending the benefits of advanced protein therapeutics to resource-limited settings.

Metal-organic frameworks (MOFs) are an emerging class of nanoporous materials that are comprised of metal ions or clusters linked by organic ligands, considered to be highly attractive for a number of applications including gas and energy storage, drug delivery, catalysis, separation, chemical sensors, and environmental and life sciences. Their attractive properties include nanoporous structure with a large surface area, tunable porosity, rich organic functionality, stable shelf-life of precursor materials and excellent thermal stability. Within the emerging applications, of particular interest is the biopreservation ability of the MOFs, which is believed to rival conventional porous solids and biomaterials. When incorporated into these nanoporous materials to form MOF biocomposites, biomolecules (e.g., protein molecules) will be confined within the rigid framework structures, thus maintaining their structures and activities against denaturation and degradation conditions.

Various approaches have been developed in accordance with the present disclosure to incorporate proteins into MOFs. Among these approaches, a spontaneous biomineralization approach and a de novo approach offer several unique advantages in the context of protein stabilization: (i) the biocomposites are formed by simply incubating proteins with MOF precursors in mild aqueous solution, which is important to maintain protein activity; (ii) the proteins are embedded in a MOF crystal with pore size smaller than the protein size, not only preventing leaching but also taking advantage of the small pore size of MOFs for specific small molecular adsorption and separation; (iii) these approaches are universal for different types of proteins since proteins serve as nucleation sites and promote MOF crystallization. The de novo approach has been employed to encapsulate enzymes for biocatalysis applications. As described herein, in some embodiments, MOFs (e.g., ZIF-8) are used as a highly effective protective materials for encapsulation and to preserve the biorecognition capabilities of antibodies or viral protein on biosensor surfaces (e.g., plasmonic nanotransducers) and to preserve the structural integrity of protein biomarkers in various biospecimens (urine, serum and plasma) that are exposed to elevated temperatures for extended duration. In some embodiments, the preserved antibody-based biosensor is restored at a later time (before use for detection) by dissociating the ZIF-8 layer in an aqueous solution at pH 6. Considering the versatile molecular encapsulation capability of ZIF-8 in aqueous solution, high thermal stability, and ability to be disintegrated upon demand by lowering the pH, ZIF-8 serves as a protective encapsulant for preserving the structure of various biofluid components (e.g., protein biomarkers, viral proteins, antibodies) under unregulated temperatures.

In some embodiments of the present disclosure, the MOF is a Materials of Institut Lavoisier (MIL) type MOF.

Novel techniques for preparing and preserving various components of a biological sample are disclosed herein. In some embodiments, protein biomarkers in biofluids (e.g., urine, serum, plasma and blood) are preserved in a dry state by combining MOF-based preservation with dry spot sample collection. The technology introduced herein involves mixing of biofluid samples with MOF precursors (e.g., ZIF-8 precursors) and drop-casting of a specific volume of the mixture onto a substrate (e.g., a paper or cellulose substrate) to allow drying of the mixture. In some embodiments, the drying process is accomplished by air drying, using a heat gun or other heating element to dry the mixture on the substrate, or any other suitable drying process in accordance with the present disclosure. In some embodiments, using a heating element to dry the mixture on the substrate is preferred to decrease drying time, particularly when the MOF encapsulant is configured to protect the target analyte/protein from heat.

In some embodiments of the present disclosure, the substrate and/or target analyte are stored at a temperature of from about −20° C. to about 100° C., from about 10° C. to about 80° C., from about 20° C. to about 60° C., about 40° C., or about room temperature. In some embodiments, the substrate and/or target analyte is stored for at least 1 week, at least 2 weeks, at least 3 weeks, at least 4 weeks, at least 6 months, at least 1 year, or at least 5 years. For example, for proteins stored at room temperature, in some embodiments no degradation occurs after 4 weeks. In some embodiments, the target analyte remains stable over many months and years.

This easily deployable process results in encapsulation of protein biomarkers within ZIF-8 crystals that could be easily dissociated upon demand at a later time. The technique overcomes the drawbacks of conventional dry spot technology (i.e. limited stability of the dried specimen, the need for refrigeration and inaccuracy in determining the concentration of the biomarker) while retaining transportation and storage convenience (FIG. 1A and FIG. 1B). By combining MOF encapsulation and dry spot sample collection, protein biomarkers (and/or other target analytes) are preserved on a paper substrate under non-refrigerated conditions. Before bioanalysis, the MOF-encapsulated proteins are recovered without losing structure and function. Neutrophil gelatinase-associated lipocalin (NGAL), a urinary biomarker for acute kidney injury, and CA-125, a serum/plasma biomarker for ovarian cancer served as the model proteins. Using the commonly employed bioanalytical tools such as enzyme-linked immunosorbent assay (ELISA), circular dichroism spectroscopy and fluorescent protein microarray, ZIF-8 encapsulation confers excellent structural stability to protein biomarkers in biospecimen in dry state, even when stored at nominal room temperature or high ambient temperatures encountered in different parts of the world. Such a biospecimen technology will not only alleviate huge financial and environmental burdens associated with "cold chain" but also extend biomedical research benefits to underserved populations by acquiring clinical samples from regions/populations currently inaccessible.

A novel biospecimen preservation approach involving the use of MOFs encapsulants (e.g., a nanoporous material such as ZIF-8) for preserving proteins (e.g., protein biomarkers) in biofluids under non-refrigerated storage conditions is disclosed herein. Using urinary NGAL and serum/plasma CA-125 as the model (or target) protein biomarkers, MOF-based encapsulants preserve protein biomarkers in urine, serum, plasma and blood at room temperature and 40° C., with comparable or better preservation efficacy than the refrigeration method (freezing liquid samples at −20° C.). In some embodiments, the protein is recovered by dissociating the protective MOF encapsulant layer in pH 6 buffer without affecting the protein structural integrity and downstream analysis. By combining the MOF-based preservation approach with dry spot sample collection method, the protein biomarker in biofluid is preserved in a dry state, greatly improving the biofluid-related biospecimen collection and handling capability in resource-limited settings. Overall, this energy-efficient and environmentally-friendly approach not only represents a novel technique to eliminate the "cold chain" and temperature-controlled handling of biofluid-related biospecimens, but also allows interruptible, storable, and restorable on-demand analysis at a later time in a centralized or distributed location/manner to improve the reliability of the bioanalytical results.

This facile and low-cost approach opens up new avenues in both research settings and clinical settings, such as large-scale cancer screenings, epidemiologic studies from tropical and disaster-struck areas, remote chronic disease monitoring and clinical trials for new drugs. A system (e.g., a "Biopreservation Kit") containing MOFs (or MOF precursors) and other materials (such as paper strips and transfer pipettes) enables patients to self-prepare dried blood/urine samples and send to hospitals or clinical labs via regular mailing. Ultimately, in some embodiments this approach alleviates hospital and logistical burdens, facilitate disease monitoring and patient feedback, and offer new services for currently underserved populations.

Further, ZIF-8 encapsulation preserves the structure and bioactivity of insulin under various environmental stressors including elevated temperature, organic solvent and mechanical agitation. Apart from standard bioanalytical tool (ELISA), CD measurements provide direct evidence for the preserved secondary structure of insulin upon ZIF-8 encapsulation. As disclosed herein, in some embodiments, the preserved protein therapeutic (e.g., insulin) bioactivity is evaluated in vivo using a diabetic mouse model. ZIF-8 encapsulated insulin at an elevated temperature (40° C.) shows comparable bioactivity to insulin stored at −20° C. The ZIF-8 residues exhibit low cytotoxicity and do not cause any side effects to animals, and in some embodiments are completely removed by a purification step before insulin administration. Overall, in some embodiments this facile approach is generalized to various protein therapeutics, thus extending the benefits of advanced protein therapeutics to resource-limited settings and under-served populations/regions. In some embodiments, this technique is easily extended to other protein therapeutics and MOFs, as demonstrated by the preserved the bioactivity of insulin with ZIF-8 encapsulation described herein.

Preserving Agents

Figure 2:
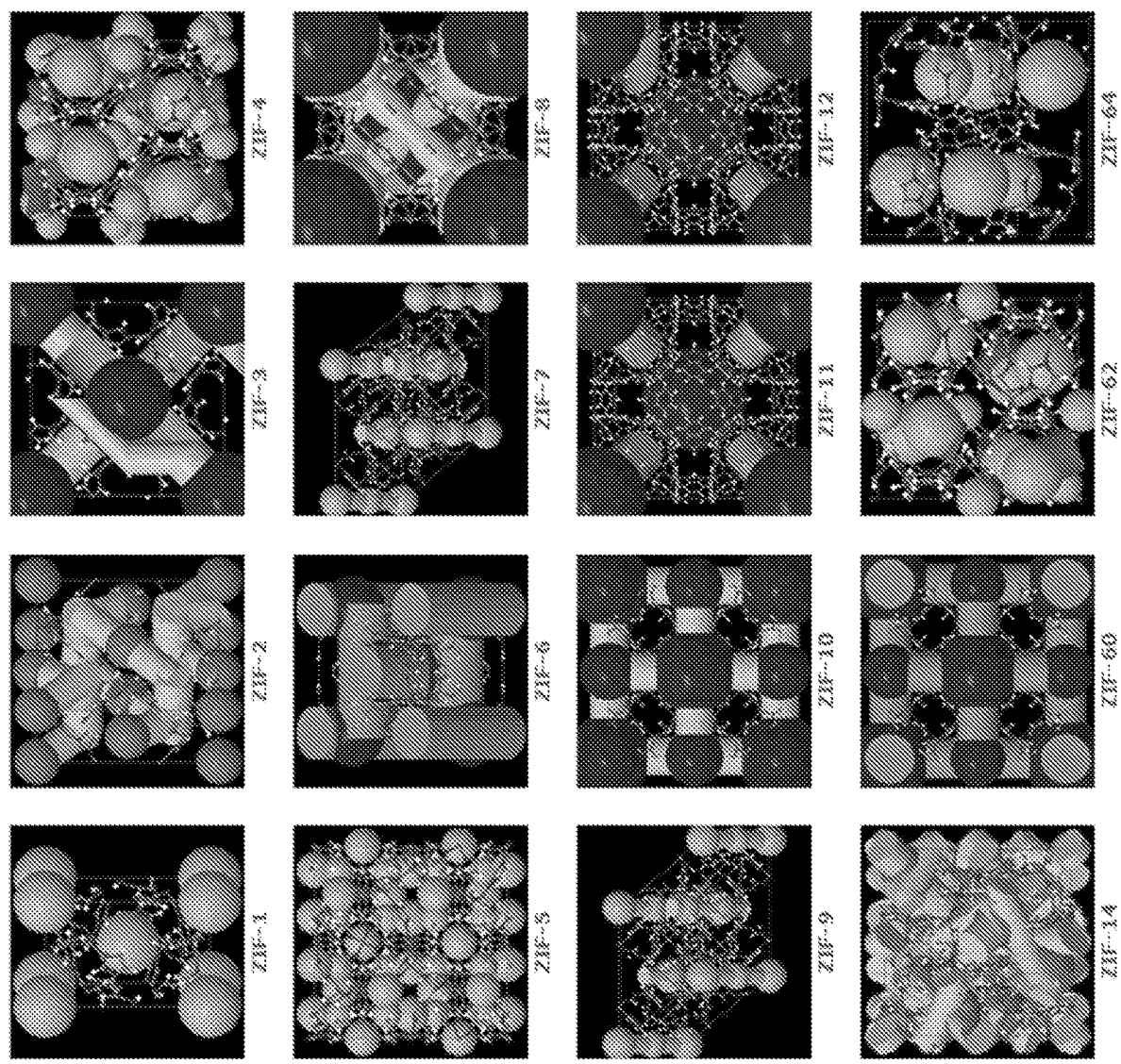
FIG. 2 depicts an exemplary embodiment of various ZIF types in accordance with the present disclosure.

As described herein, a preserving agent comprises an encapsulant configured to encapsulate, preserve, and/or protect various target analytes in a biological sample. The preserving agent is selected from a metal-organic framework (MOF) encapsulant or a precursor or precursors forming an MOF encapsulant. Exemplary MOF encapsulants in accordance with the present disclosure include ZIF (zeolitic imidazolate framework) type and MIL (Materials of Institut Lavoisier) type MOFs. For example, ZIFs are a class of metal-organic frameworks that are topologically isomorphic with zeolites. In some embodiments, ZIFs are composed of tetrahedrally-coordinated transition metal ions (e.g. Fe, Co, Cu, Zn) connected by imidazolate linkers. Because the metal-imidazole-metal angle is similar to the 145° Si—O—Si angle in zeolites, in some embodiments the ZIFs have zeolite-like topologies. FIG. 2 shows various examples of ZIFs. In some embodiments, MOF precursors comprise ZIF or MIL precursors. For example, in some embodiments, the precursor forming the MOF encapsulant comprises 2-methylimidazole and zinc acetate, which are precursors to ZIF-8.

Target Analytes

Biological samples in accordance with the present disclosure, such as biofluids, include, but are not limited to, urine, blood, serum, plasma, saliva, cerebrospinal fluid, and any other biological fluid. Target analytes include biomarkers, protein biomarkers, protein therapeutics, antibodies, viruses, viral proteins, oligonucleotides, DNA, RNA, macromolecules having a primary structure and a secondary structure, proteins having an amino acid sequence from an organism, polypeptides having an amino acid sequence from an organism, and any other substance of interest to be analyzed that are present in a biological sample. Protein biomarkers include neutrophil gelatinase-associated lipocalin (NGAL), kidney injury modecule-1 (KIM-1), albumin, beta-2 microglobulin, cystatin C, cancer antigen 125 (CA-125), prostate-specific antigen (PSA), human IgG and IgM, ZIKV nonstructural protein 1, cytokines, and any other protein biomarker present in the biological sample. Protein therapeutics include, but are not limited to, insulin, monoclonal antibodies, erythropoietin, cytokines, vaccines, and any other protein therapeutic present the biological sample.

Systems for Preparing and Preserving Biological Samples

Systems for preparing and preserving various biological samples (or components of biological samples) facilitate performance of the methods described herein. In some embodiments, a system comprises at least one preserving agent or composition as described herein configured to encapsulate at least one target analyte of a biological sample, a substrate or matrix configured to receive the encapsulated target analyte and, in some embodiments, instructions for administration. Such kits can. When supplied as a kit, components (preserving agents and substrates) are packaged and stored in separate containers until use. Components include, but are not limited to a preserving agent (e.g., MOFs and MOF precursors), a substrate/matrix (e.g., cellulose and non-cellulose sample coupons/strips), storage containers, transfer pipettes, shipping containers, and postage. In some embodiments, the substrate comprises any water insoluble material, such as, for example, any fibrous material.

System/kit components enable patients to self-prepare biological samples (e.g., dried blood/urine samples) and send to hospitals or clinical labs (e.g., via regular mailing). In some embodiments, such packaging of the components separately is presented in a pack or dispenser device which contains one or more unit dosage forms containing the composition. In some embodiments, the pack comprises metal or plastic foil such as a blister pack. Such packaging of the components separately, in certain instances, permits long-term storage without losing activity of the components.

In some embodiments, systems/kits include reagents in separate containers such as, for example, sterile water or saline to be added to a lyophilized active component packaged separately. For example, in some embodiments sealed glass ampules contain a lyophilized component and in a separate ampule, sterile water or sterile saline each of which has been packaged under a neutral non-reacting gas, such as nitrogen. Ampules consist of any suitable material, such as glass, organic polymers, such as polycarbonate, polystyrene, ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, and the like. In some embodiments, containers have a sterile access port, such as a bottle having a stopper that are pierced by a hypodermic injection needle. In some embodiments, containers have two compartments that are separated by a readily removable membrane that upon removal permits the components to mix. Removable membranes include glass, plastic, rubber, and the like.

In some embodiments, systems/kits are supplied with instructional materials. In some embodiments, instructions are printed on paper or other substrate, and/or are supplied as an electronic-readable medium, such as a floppy disc, mini-CD-ROM, CD-ROM, DVD-ROM, Zip disc, videotape, audio tape, and the like. In some embodiments, detailed instructions are not physically associated with the kit; instead, a user is directed to a specified web site or app (e.g., a web site or app hosted/provided by the manufacturer or distributor of the kit).

Compositions and methods described herein utilizing molecular biology protocols can be performed according to a variety of standard techniques known to the art. Definitions and methods described herein are provided to better define the present disclosure and to guide those of ordinary skill in the art in the practice of the present disclosure without limiting the scope of the disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus are considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Preparation and Characterization of ZIF-8 Encapsulated NGAL

Figure 3:
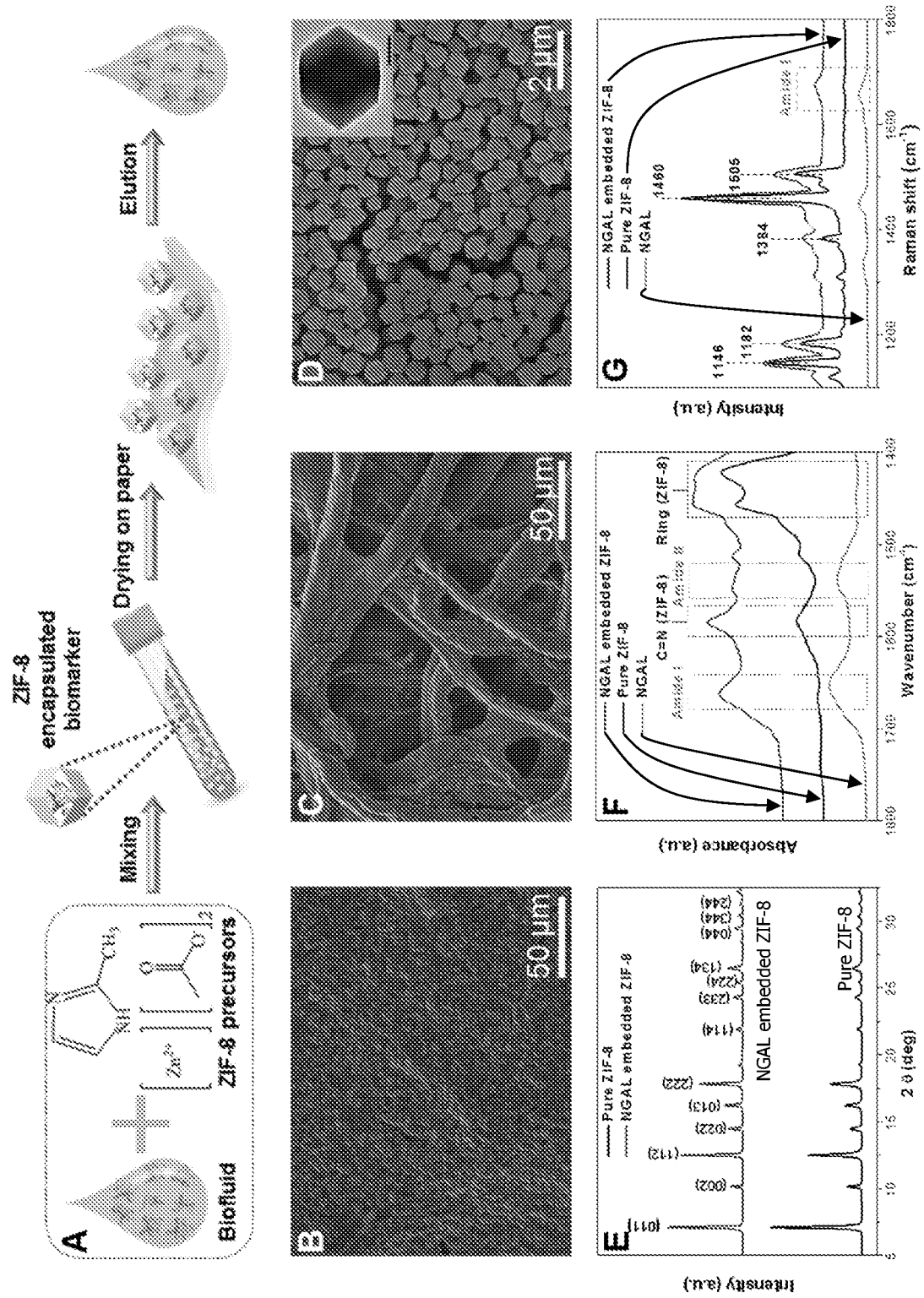
FIG. 3A depicts an exemplary embodiment of a schematic illustrating the sample preparation of ZIF-8 encapsulated biofluid on a paper substrate in accordance with the present disclosure.
FIG. 3B depicts an exemplary embodiment of a SEM image of a paper substrate after drying NGAL-spiked artificial urine with ZIF-8 precursors in accordance with the present disclosure.
FIG. 3C depicts an exemplary embodiment of a SEM image of a paper substrate after drying NGAL-spiked artificial urine without ZIF-8 precursors in accordance with the present disclosure.
FIG. 3D depicts an exemplary embodiment of a SEM image of NGAL-embedded ZIF-8 crystals showing uniform size and shape in accordance with the present disclosure.
FIG. 3E depicts an exemplary embodiment of an XRD pattern of pure ZIF-8 and NGAL-embedded ZIF-8 crystals in accordance with the present disclosure.
FIG. 3F depicts an exemplary embodiment of a FTIR spectra of NGAL, pure ZIF-8 and NGAL-embedded ZIF-8 crystals in accordance with the present disclosure.
FIG. 3G depicts an exemplary embodiment of Raman spectra of NGAL, pure ZIF-8 and NGAL-embedded ZIF-8 crystals in accordance with the present disclosure.
Figure 4:
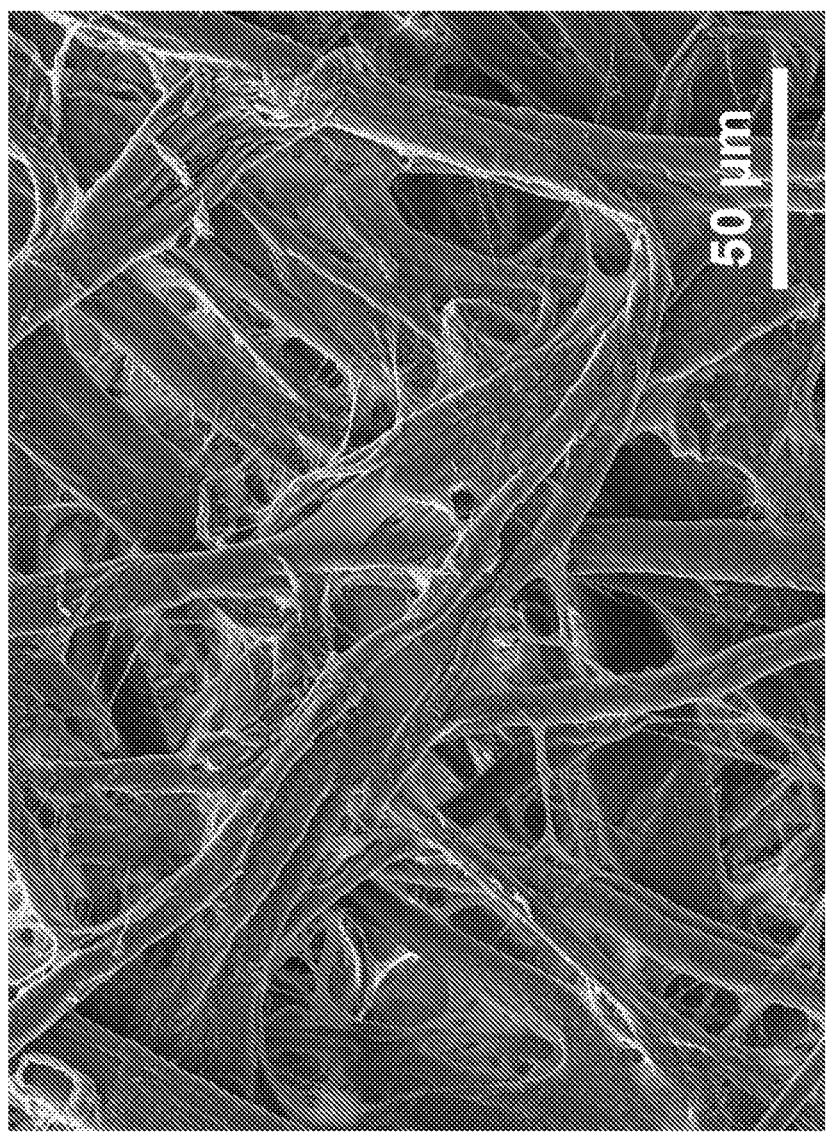
FIG. 4 depicts an exemplary embodiment of a SEM image of bare Whatman 903 paper in accordance with the present disclosure.
Figure 5:
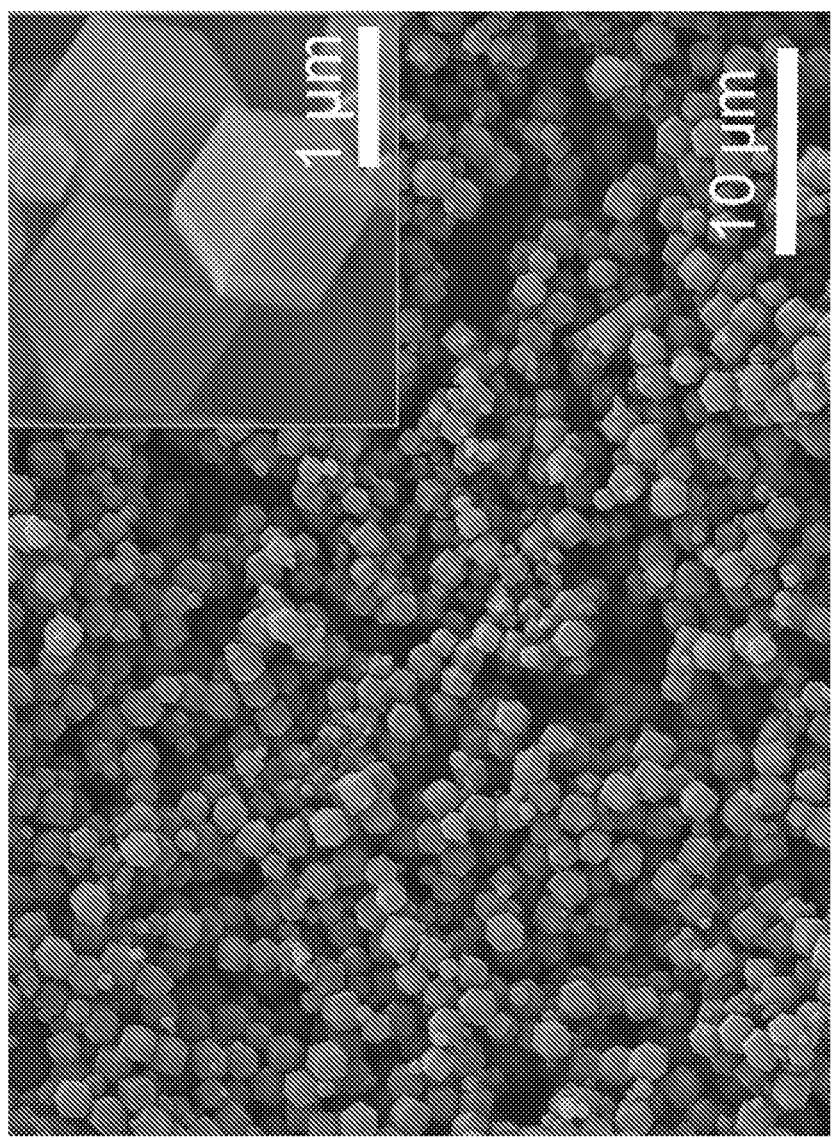
FIG. 5 depicts an exemplary embodiment of SEM images of pure ZIF-8 in accordance with the present disclosure.

NGAL-spiked artificial urine was employed as a model biospecimen. To prepare a typical ZIF-8 preserved sample, NGAL-spiked artificial urine (50 µg/ml, 25 µl) was first mixed with 2-methylimidazole solution (640 mM, 12.5 µl) and then zinc acetate solution (160 mM, 12.5 µl), and incubated at room temperature for 1 hour. Subsequently, the mixture (50 µl) was air-dried on a 0.5×2 cm Whatman 903 paper strip (which usually takes 2 hours at room temperature) (FIG. 3A). Scanning electron microscope (SEM) images show the distinct morphologies of paper substrates after drying NGAL-spiked artificial urine with and without ZIF-8 precursors (FIGS. 3B and 3C). The granular morphology of the paper substrate with artificial urine mixed with ZIF-8 precursors suggests the formation of ZIF-8 crystals (FIG. 3B). Conversely, the morphology of the sample without adding ZIF-8 precursors (FIG. 3C) is similar to bare paper (FIG. 4) since the proteins are too small to be visible at this magnification. Owing to their rich functionality (such as carboxyl, carbonyl, hydroxyl, and imidazole groups), proteins serve as nucleation sites for the formation of ZIF-8 crystals. ZIF-8 crystals form and encapsulate NGAL in the presence of ZIF-8 precursors in the NGAL-spiked artificial urine. The NGAL-embedded ZIF-8 crystals formed after 1 hour incubation of the mixture solution and could be collected by centrifugation. The SEM and transmission electron microscopy (TEM) images show that the crystals formed in the NGAL-spiked artificial urine exhibit uniform size of $\infty$0.5 µm (FIG. 3D; Inset: TEM image of a typical NGAL-embedded ZIF-8 crystal; Scale bar: 200 nm), with a rhombic dodecahedral shape, similar to that of pure ZIF-8 crystals (FIG. 5). The powder X-ray diffraction (XRD) pattern of the crystals also exhibits the typical peaks of pure ZIF-8 crystals (FIG. 3E).

Figure 6:
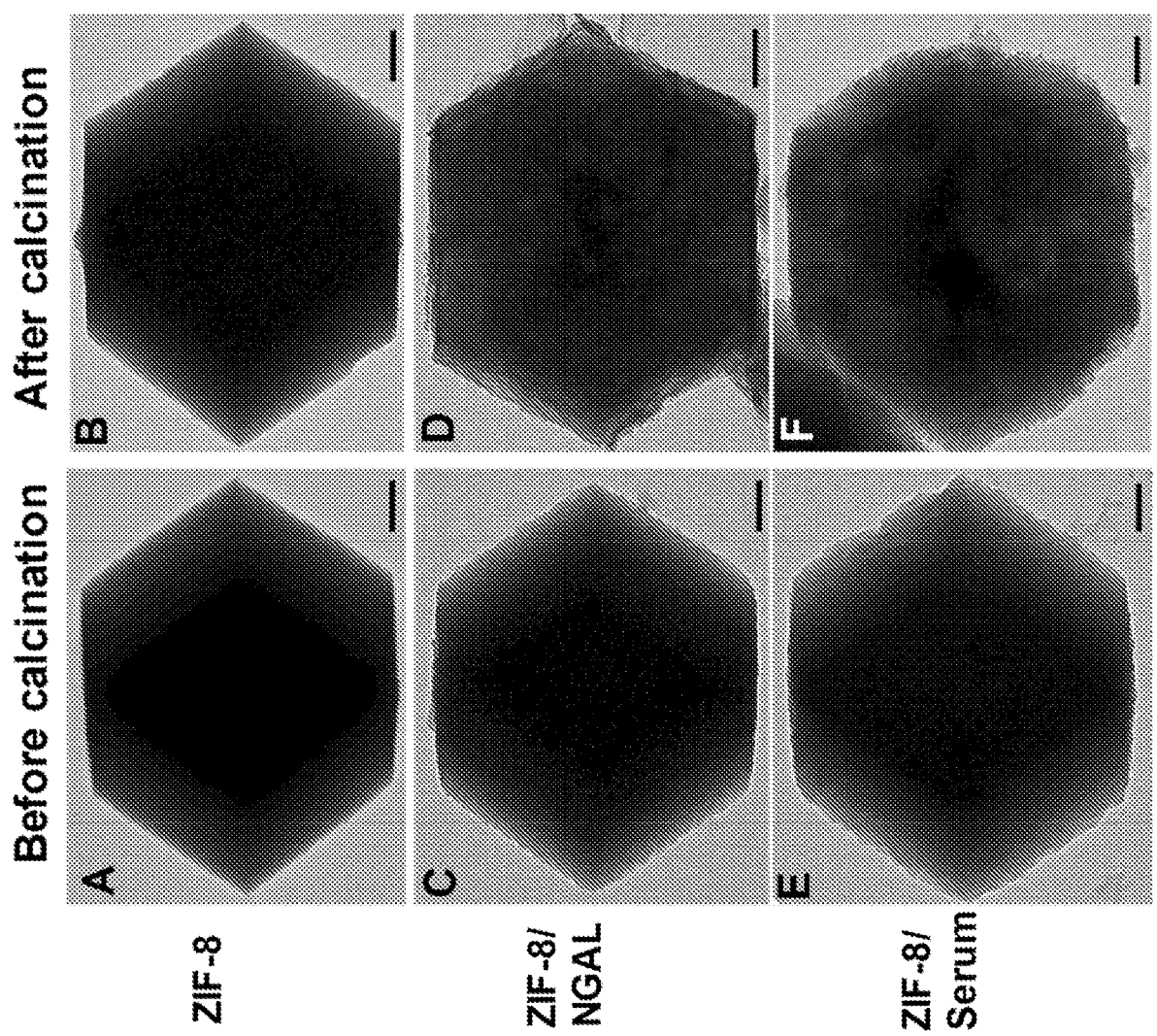
FIG. 6 depicts an exemplary embodiment of TEM images before and after calcination of pure ZIF-8 (A and B), NGAL-embedded ZIF-8 (C and D) and serum-embedded ZIF-8 (20-fold diluted serum, (E and F) crystals in accordance with the present disclosure.

To confirm the encapsulation of NGAL into ZIF-8 crystals, both pure ZIF-8 and NGAL-embedded ZIF-8 crystals were subjected to calcination (325° C. for 2 h). Only NGAL-embedded ZIF-8 showed pores in the calcinated crystals, indicating the encapsulation of protein in the ZIF-8 crystals (FIG. 6; Scale bars: 100 nm). To further ascertain the formation of NGAL-embedded ZIF-8 crystals, Fourier transform infrared spectroscopy (FTIR) and Raman spectroscopy were employed. The FTIR spectrum obtained from the crystals not only shows typical ZIF-8 absorption peaks at 1584 cm-1 (C$=$N stretching of imidazole) and 1400-1500 cm-1 (the imidazole ring stretching), but also exhibits absorption peaks at 1640-1670 and 1520-1560 cm-1, corresponding to amide I and amide II bands of protein, respectively (FIG. 3F). In contrast, pure ZIF-8 crystals and NGAL only show their respective characteristic peaks. Similar results are observed by Raman spectroscopy, which also indicates the encapsulation of NGAL by ZIF-8 crystals (FIG. 3G). The Raman spectrum obtained from pure NGAL exhibits a broad band at 1630-1690 cm-1, corresponding to amide I band of protein. The NGAL-encapsulating ZIF-8 crystals exhibit the amide I band of NGAL (not present in pure ZIF-8 crystals) and 2-methylimidazole characteristic bands at 1146, 1182, 1384, 1460 and 1505 cm-1 corresponding to C—N stretching, C—N stretching plus N—H wagging, CH3 bending, C—H wagging and C—N stretching plus N—H wagging, respectively.

Example 2: Recovery of NGAL from ZIF-8 Encapsulation

Figure 7:
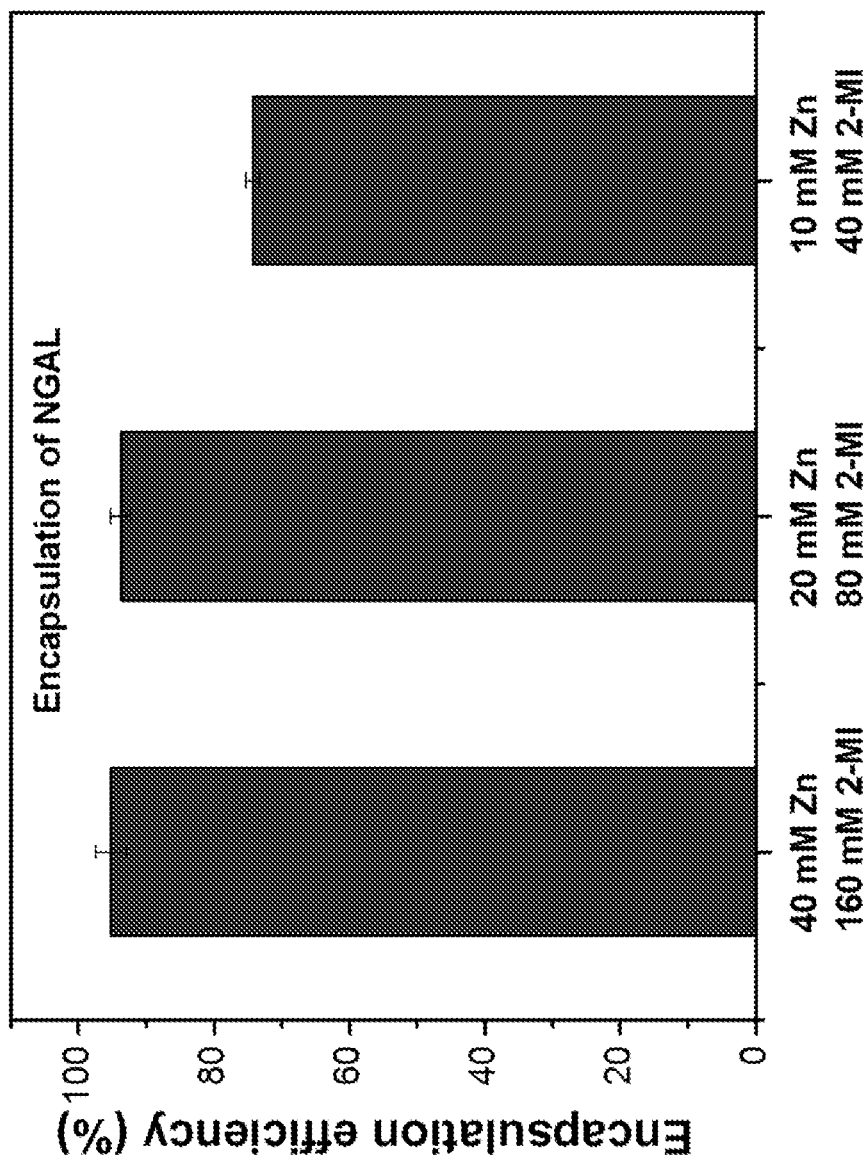
FIG. 7 depicts an exemplary embodiment of encapsulation efficiency of NGAL spiked in artificial urine (50 µg/ml) using three different concentrations of ZIF-8 precursors in accordance with the present disclosure.

To quantify the encapsulation efficiency, the supernatant after crystals centrifugation was collected and remaining NGAL concentration was determined using sandwich enzyme-linked immunosorbent assay (ELISA). The encapsulation efficiency was found to be dependent on the concentration of ZIF-8 precursors. Specifically, when the concentrations of zinc acetate and 2-methylimidazole in the mixture increased to 40 mM and 160 mM, respectively, ~95% NGAL was encapsulated within ZIF-8 crystals (FIG. 7). The encapsulation efficiency was calculated by subtracting the remaining NGAL amount in the supernatant after encapsulation and centrifugation (concentration measured by ELISA) from the total NGAL amount. Results are the mean and standard deviation from three independent experiments. As a control experiment, mixing of NGAL-spiked artificial urine with pure ZIF-8 crystals resulted in extremely low (~10%, owing to the physical adsorption) encapsulation efficiency. This physical mixing of pre-formed ZIF-8 crystals with the protein biomarkers is in stark contrast with the protein-embedding approach (i.e. formation of ZIF-8 crystals in the presence of protein biomarkers), which exhibited high encapsulation efficiency (95%).

Example 3: Preservation of NGAL Spiked in Artificial Urine

Figure 8:
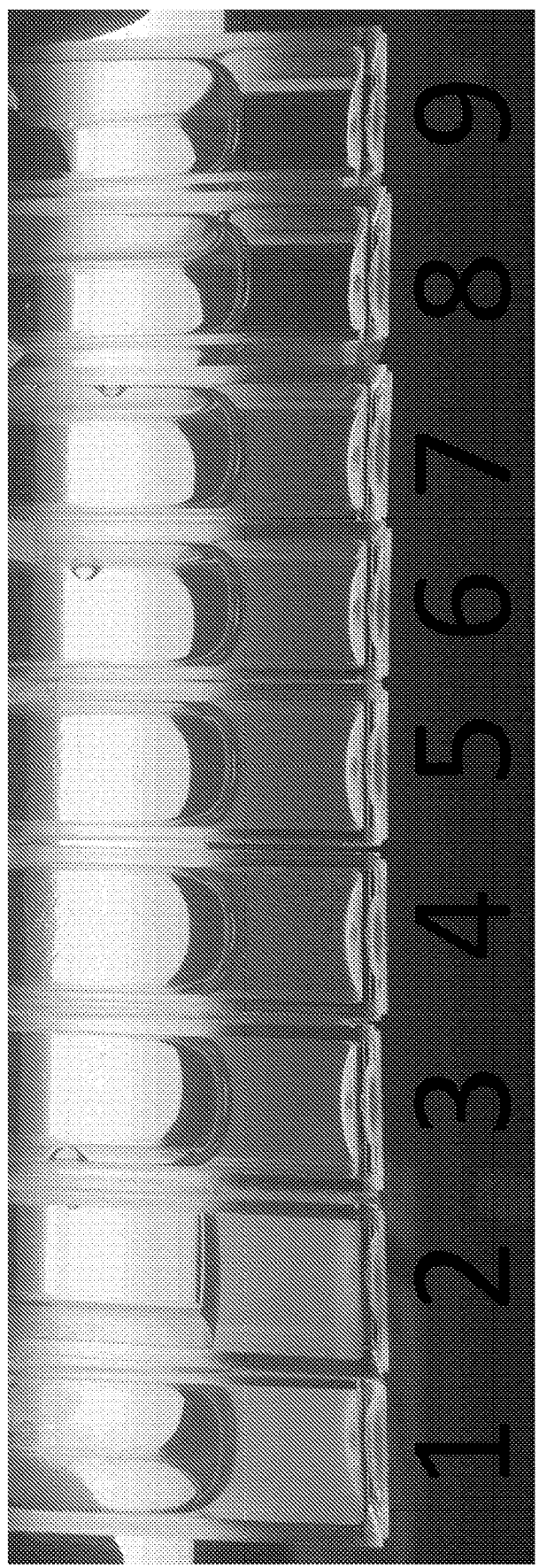
FIG. 8 depicts an exemplary embodiment of preliminary experiments for investigating optimal buffer to dissolve NGAL embedded ZIF-8 crystals in accordance with the present disclosure.

Preliminary experiments for investigating optimal buffer to dissolve NGAL embedded ZIF-8 crystals. To completely dissolve the crystals, the final pH of the system needs to be at or below 6.0 to ensure the complete release of NGAL from ZIF-8 encapsulation. For example, in the #4 composition (0.1 M phosphate buffer at pH 6.0), the crystals cannot be completely dissolved and this leads to incomplete recovery 60%, FIG. 8). Although the initial pH of the buffer is 6.0, the basic nature of ZIF-8 precursor residue in the system increases the pH of the buffer to 6.2, leading to incomplete release and recovery. In the case of the #9 composition, NGAL-embedded ZIF-8 crystals completely dissolve within 5 minutes, and over 95% of encapsulated NGAL is recovered (FIG. 8).

Figure 9:
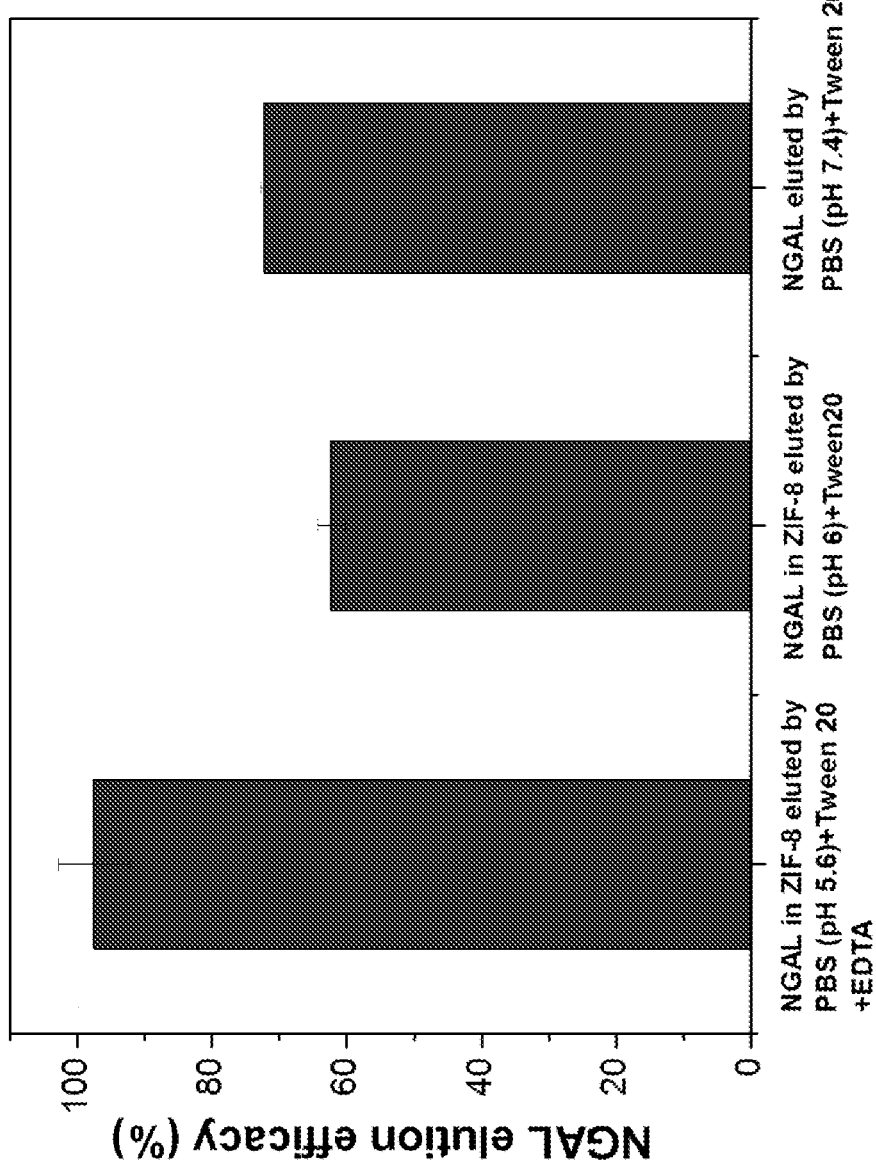
FIG. 9 depicts an exemplary embodiment of elution efficacy of NGAL alone or ZIF-8-encapsulated NGAL from paper substrates in accordance with the present disclosure.

FIG. 9 shows elution efficacy of NGAL alone or ZIF-8-encapsulated NGAL from paper substrates. Left bar: Recovery percentage of ZIF-8 encapsulated NGAL dried on paper using the optimized elution buffer (#9 composition, 0.2 M PBS at pH=5.6 with 2 mM EDTA and 0.1% Tween 20). Middle bar: Recovery percentage of ZIF-8 encapsulated NGAL dried on paper using the #4 composition elution buffer (0.1 M PBS at pH=6 and 0.1% Tween 20). Right bar: Recovery percentage of NGAL alone dried on paper using the conventional elution buffer recipe (PBS at pH=7.4 with 0.1% Tween 20). The samples were recovered immediately after drying. 1 ml elution buffer was used to elute each paper strip. The spiked NGAL amount was set as the reference (100% recovery).

The efficacy was evaluated of ZIF-8 encapsulation in preserving NGAL upon exposure to harsh conditions (such as elevated temperatures) that would normally lead to protein denaturation and loss of biospecimen integrity. NGAL-spiked artificial urine dried on paper substrates, both with and without ZIF-8 encapsulation, was stored at 25, 40, or 60° C. for 1 week. Before analysis, the optimized elution buffer (0.2 M phosphate buffer at pH 5.6+Tween 20+EDTA, see Table 1 and FIGS. 8 and 9 for details) was used to elute NGAL from the paper substrates.

TABLE 1

Elution buffers.

| Composition | Transparency in 5 minutes | Final pH |
| --- | --- | --- |
| Deionized water (pH 7.2) | cloudy | 8.6 |
| Deionized water (pH 5.9) | cloudy | 7.8 |
| Phosphate buffered saline (PBS, pH 7.4) | cloudy | 7.6 |
| 0.1M phosphate buffer (pH 6) | cloudy | 6.2 |
| 0.1M phosphate buffer (pH 5.6) | cloudy | 5.9 |
| 0.15M phosphate buffer (pH 5.6) | cloudy | 5.7 |
| 0.2M phosphate buffer (pH 5.6) | cloudy | 5.7 |
| 0.5M phosphate buffer (pH 6) | clear | 6 |
| 0.2M phosphate buffer + 2 mM EDTA (pH 5.6) | clear | 5.7 |

Figure 10:
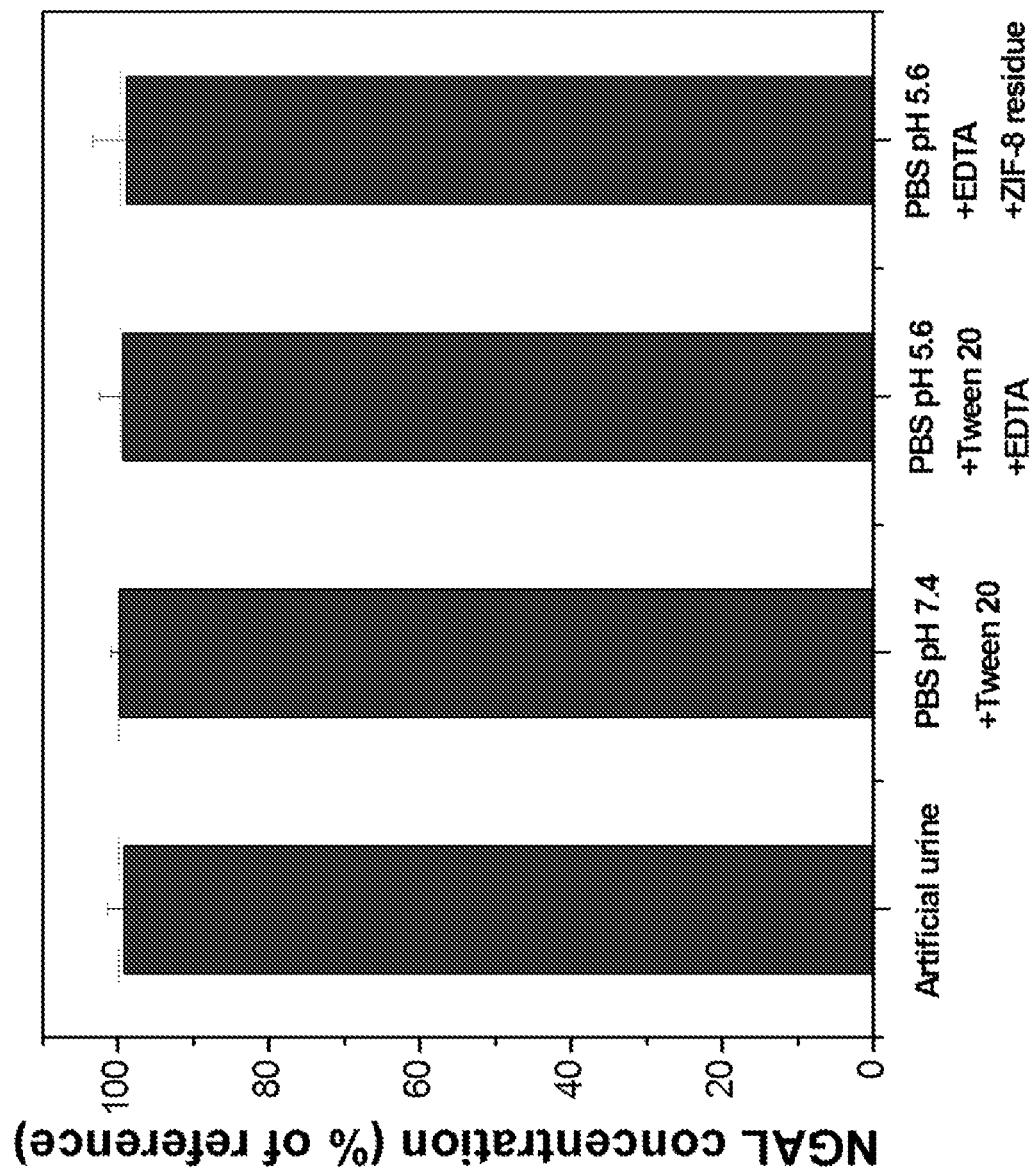
FIG. 10 depicts an exemplary embodiment of the investigation of adaptability of sample matrix (artificial urine), elution buffer or ZIF-8 residue to the downstream analysis in accordance with the present disclosure.
Figure 11:
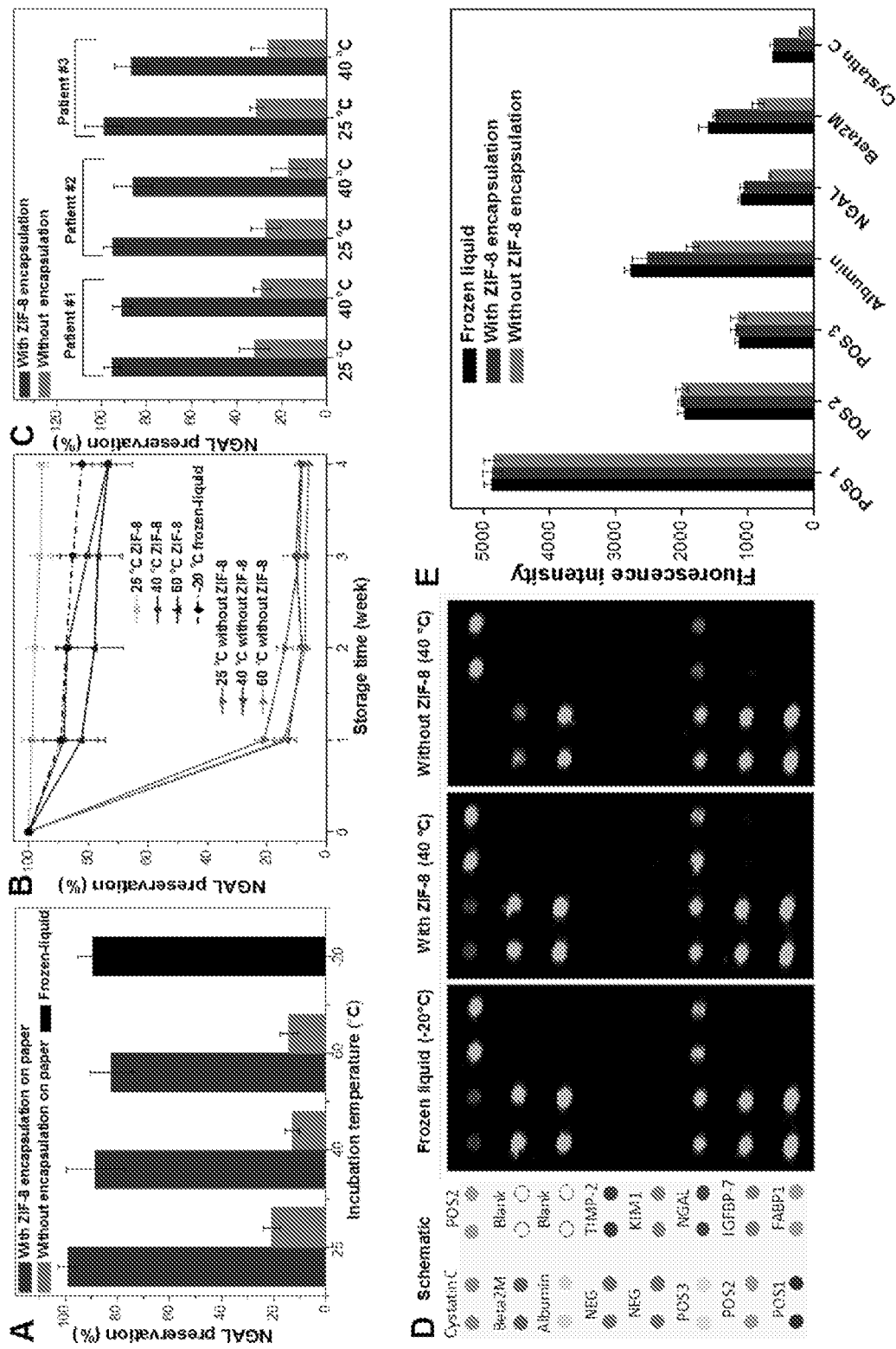
FIG. 11A depicts an exemplary embodiment of preservation efficacy of NGAL with and without ZIF-8 encapsulation in accordance with the present disclosure.
FIG. 11B depicts an exemplary embodiment of preservation efficacy of NGAL on paper cards in accordance with the present disclosure.
FIG. 11C depicts an exemplary embodiment of preservation efficacy of NGAL in patient urine in accordance with the present disclosure.
FIG. 11D depicts an exemplary embodiment of fluorescence intensity maps in accordance with the present disclosure.
FIG. 11E depicts an exemplary embodiment of a plot depicting the fluorescence intensity of various biomarkers for the samples described in FIG. 11D in accordance with the present disclosure.
Figure 12:
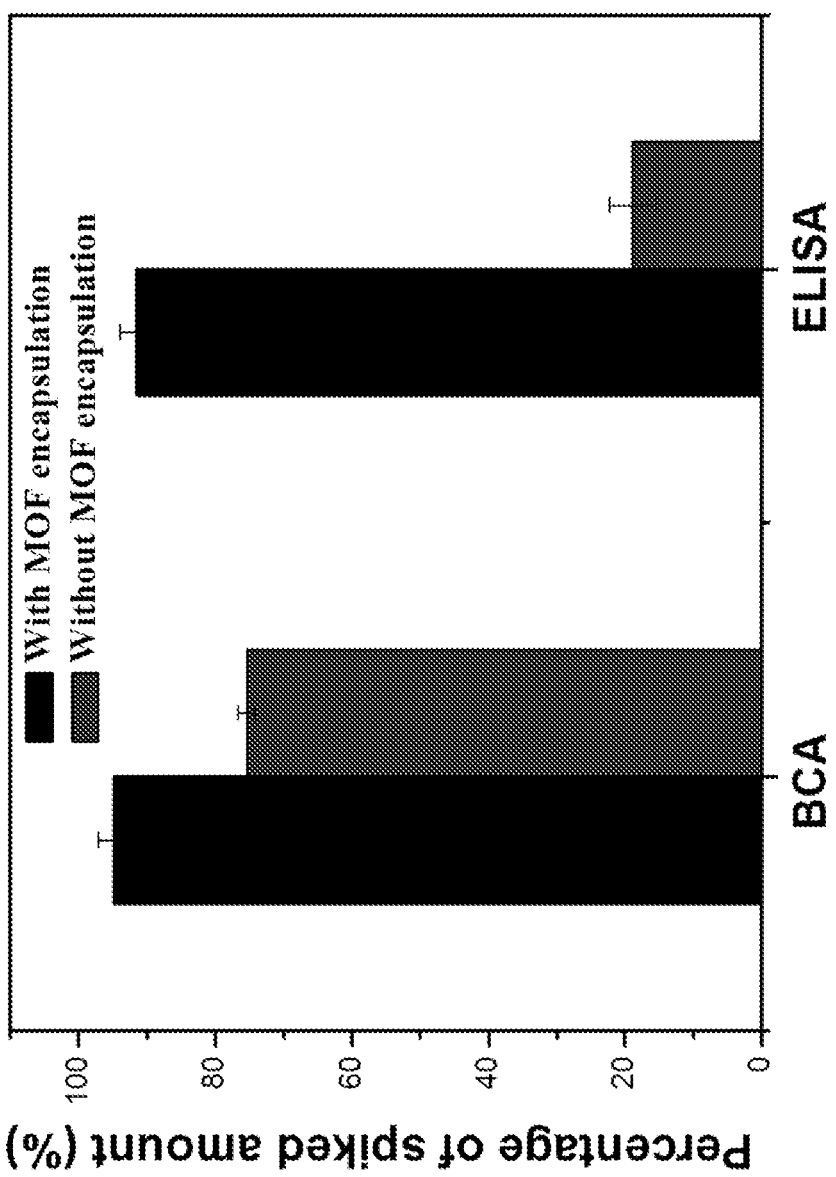
FIG. 12 depicts an exemplary embodiment of NGAL quantity (expressed in terms of % of spiked amount) in eluates using BCA and ELISA in accordance with the present disclosure.
Figure 13:
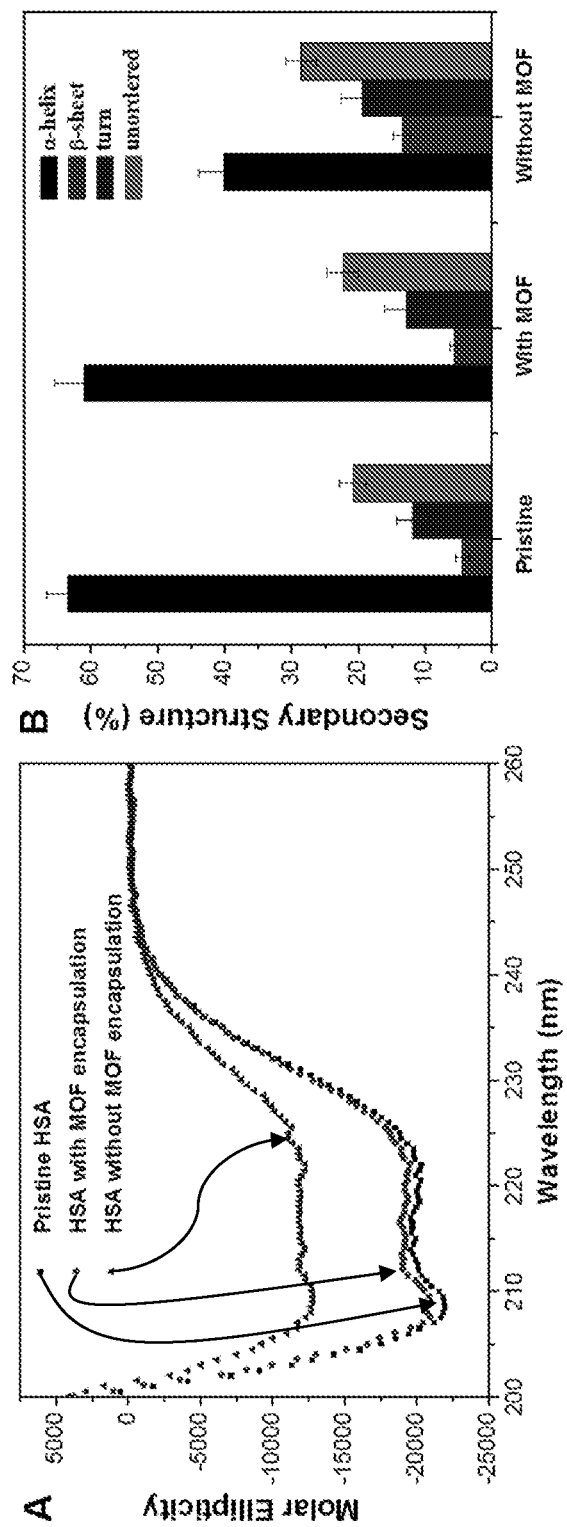
FIG. 13A depicts an exemplary embodiment of circular dichroism (CD) spectra in accordance with the present disclosure.
FIG. 13B depicts an exemplary embodiment of secondary structure content of the three types of HSA obtained from the CD spectra in accordance with the present disclosure.

The slightly acidic environment (at or below pH 6) was employed to dissociate ZIF-8 crystals and release encapsulated NGAL via breaking coordination between the zinc ions and imidazolate. ZIF-8 encapsulated NGAL dried on the paper was almost fully eluted (>95%) whereas NGAL alone dried on the paper was only partially eluted (~75%) (FIG. 9). It is important to note that ZIF-8 encapsulation prevented irreversible adsorption of proteins on the cellulose fibers by creating a crystal interface between the protein and paper substrate. The slightly acidic elution buffer and the ZIF-8 residue did not alter the protein characteristics and downstream bioanalysis (FIG. 10). NGAL concentration was tested by ELISA when NGAL was spiked in four different media. The same concentration of NGAL in phosphate-buffered saline (PBS) at pH 7.4 was set as the reference (100%). Results are the mean and standard deviation from three independent samples. The results show that the ELISA performance and NGAL characteristics are not affected by the sample matrix (artificial urine), the pH of the buffer (range from 5.6 to 7.4), the additives in the elution buffer (including Tween 20 and EDTA), and the presence of ZIF-8 residues, ascertaining that there are no false positive or negative results stemming from the recovery process. After storage and elution, the concentration of NGAL in the eluate was quantified using the NGAL sandwich ELISA. The preservation efficacy (preservation %) was calculated by comparing the NGAL amount in the eluate to the spiked NGAL amount in the artificial urine. As shown in FIG. 11A, there was more than 85% preservation of NGAL with ZIF-8 encapsulation after 1 week storage at 25 and 40° C., as well as more than 80% at 60° C. NGAL added on a paper card was stored at 25, 40 or 60° C. for one week. The ZIF-8 encapsulation shows comparable preservation, after storage at either room temperature or elevated temperatures, to the refrigeration method (freezing liquid samples at −20° C.). Notably, at 25 and 40° C., NGAL with ZIF-8 encapsulation showed comparable preservation to freeze-thawed liquid samples (the refrigeration approach as the control) stored at −20° C. On the other hand, NGAL without ZIF-8 encapsulation stored at these temperatures for 1 week exhibited less than 30% preservation although 70% of the proteins were eluted as measured by bicinchoninic acid (BCA) assay, indicating the denaturation of NGAL under these storage conditions (FIG. 12). The eluates were obtained by eluting paper cards dried with NGAL-spiked artificial urine with or without MOF encapsulation after storage at 40° C. for 1 week. Results are the mean and standard deviation from three independent samples. To further confirm that ZIF-8 encapsulation preserves the encapsulated protein structure, circular dichroism (CD) spectroscopy was employed to characterize the secondary structure of human serum albumin (HSA) with and without ZIF-8 encapsulation after 1 week incubation at 40° C. (FIG. 13A and FIG. 13B, results are the mean and standard deviation from three independent samples). FIG. 13A shows pristine human serum albumin (HSA) prior to incubation, HSA with ZIF-8 encapsulation after 1 week incubation at 40° C. and HSA without ZIF-8 encapsulation after 1 week incubation at 40° C. As expected, elevated temperature caused a significant change (a decrease in the α-helical content) of the secondary structure of unencapsulated HSA, as shown in the CD spectrum. In contrast, the secondary structure of ZIF-8 encapsulated HSA was found to be very similar to that of the pristine HSA, indicating that ZIF-8 encapsulation is able to preserve the structure of encapsulated protein.

Figure 14:
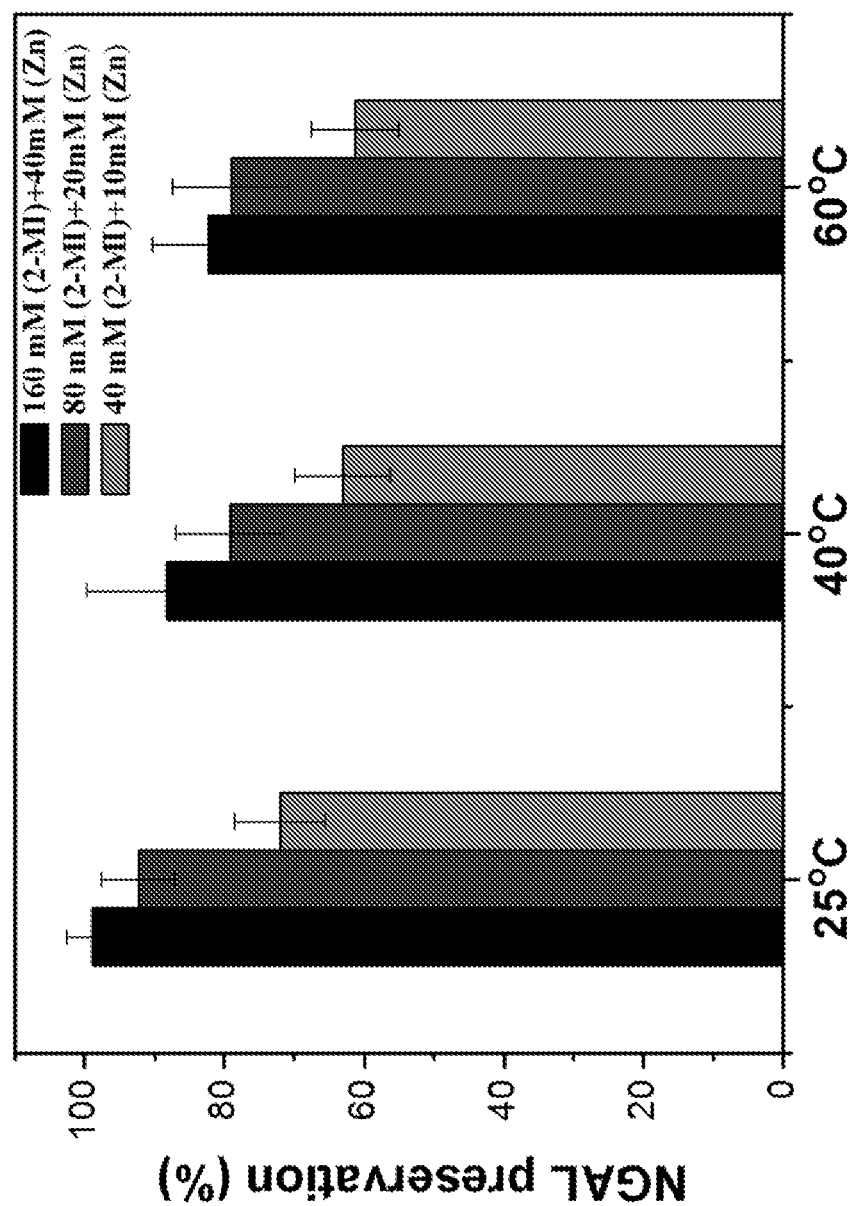
FIG. 14 depicts an exemplary embodiment of preservation efficacy of NGAL on paper cards using different concentrations of 2-methylimidazole (2-MI) and zinc acetate (Zn) in accordance with the present disclosure.

The preservation efficacy critically depended on the concentrations of 2-methylimidazole and zinc acetate (FIG. 14). FIG. 14 shows preservation efficacy of NGAL on paper card at 25, 40 or 60° C. for one week using different concentrations of 2-methylimidazole (2-MI) and zinc acetate (Zn). The maximal preservation percentage was obtained using 160 mM of 2-methylimidazole and 40 mM of zinc acetate. Results are the mean and standard deviation from three independent samples. A low preservation was noted upon using 40 mM 2-methylimidazole with 10 mM zinc acetate, which is attributed to incomplete encapsulation of NGAL under this condition (~70% encapsulation of NGAL using 40 mM 2-methylimidazole with 10 mM zinc acetate, FIG. 7). Subsequently, using the optimal ZIF-8 precursor concentration (160 mM 2-methylimidazole and 40 mM zinc acetate), the storage time was extended under different temperatures up to 4 weeks (FIG. 11B). FIG. 11B shows preservation efficacy of NGAL on paper cards at 25, 40 or 60° C. for different durations. Results are the mean and standard deviation from three independent samples. Different dried paper strips were sampled at selected time points (2, 3 or 4 weeks) to monitor possible changes in NGAL preservation. With ZIF-8 encapsulation, over 70% of NGAL on paper was preserved up to 4 weeks (the maximum time tested) at all three temperatures (25, 40 and 60° C.), as opposed to 20% preservation on samples without ZIF-8 encapsulation. Notably, the ZIF-8 encapsulation had comparable preservation (~90%, at 25 and 40° C.) to the freezing method over 2 weeks (~20° C.). Remarkably, 70% of NGAL on paper could be preserved within 4 weeks at 60° C., which represented an extremely harsh storage condition (a surrogate for long-term storage stability at room temperature).

Example 4: Preservation of Patient Urine Samples

Figure 15:
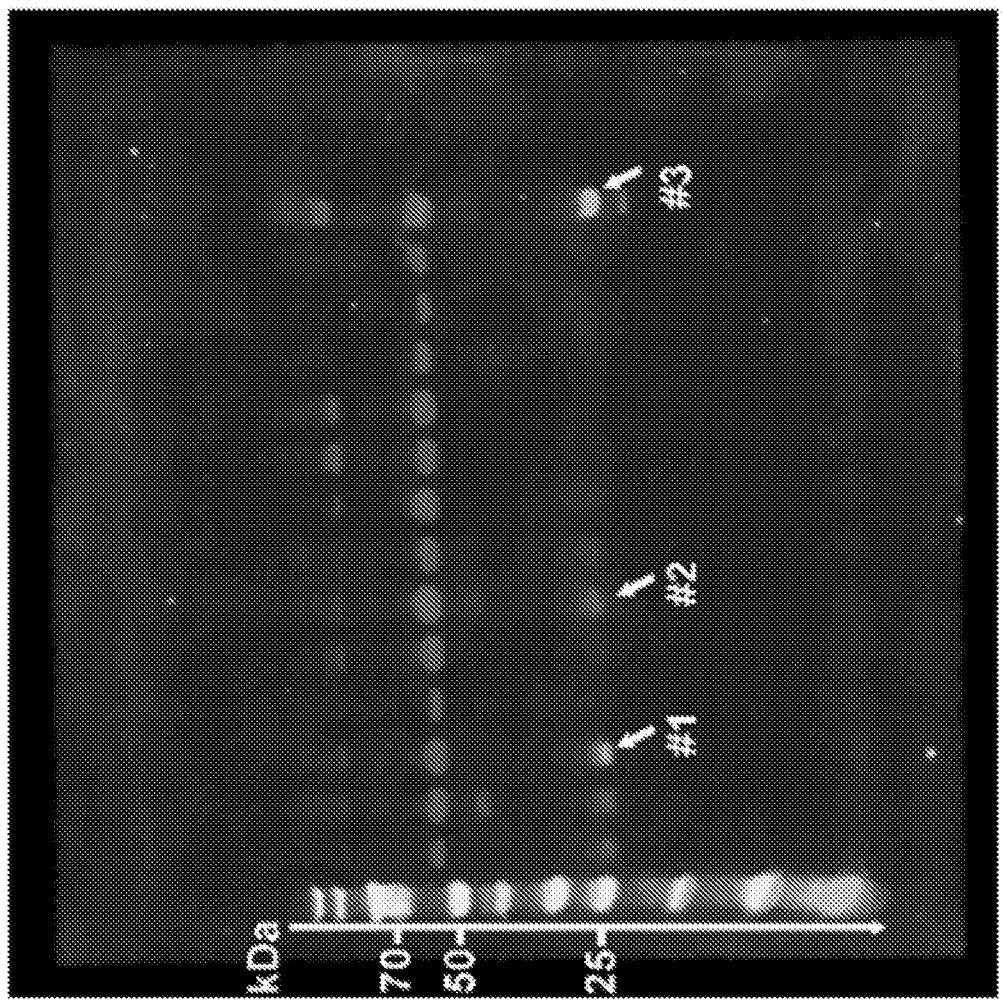
FIG. 15 depicts an exemplary embodiment of Western blot of fourteen patients' urine samples in accordance with the present disclosure.

Following the successful optimization of ZIF-8 encapsulation using spiked artificial urine samples, the applicability of this technique to patient urine samples was evaluated. Three acute kidney injury patients with different urinary NGAL levels (Patient #1: 32.8 ng/ml, Patient #2: 17.4 ng/ml and Patient #3: 97.5 ng/ml, quantified by ELISA and confirmed by Western blotting, FIG. 15) were selected. Detection with antibodies against NGAL and albumin reveals two clearly identified bands corresponding to NGAL (~25 kDa, green color bands) and albumin (~66 kDa, red color bands). To demonstrate applicability of the technique in preserving protein biomarker with different concentrations, three patients with different urinary NGAL levels (marked by white arrows) were selected for ZIF-8 encapsulation. Compared to artificial urine, human urine is more complex due to the presence of different types of proteins such as albumin and globulins, and even whole cells (e.g., red blood cells and shed kidney cells).53 As routinely done, the cells were removed by low speed centrifugation before ZIF-8 encapsulation. Mixing patient urine with ZIF-8 precursors resulted in a solution at near neutral pH. Thus, protein biomarkers in the mixture are not subjected to extremely low or high pH (Table 2). To assess the preservation efficacy of NGAL, the urine samples with and without ZIF-8 encapsulation dried on paper substrates were stored at 25 or 40° C. for 1 week. NGAL concentration in the eluate was quantified using ELISA. For all three patients, the samples with ZIF-8 encapsulation resulted in more than 85% NGAL preservation after 1 week storage at both 25 and 40° C., whereas the control samples without ZIF-8 encapsulation showed less than 40% NGAL preservation (FIG. 11C). FIG. 11C shows preservation efficacy of NGAL in urine from three acute kidney injury patients with and without ZIF-8 encapsulation on paper cards stored at 25 or 40° C. for one week. Results are the mean and standard deviation from three independent samples. To further demonstrate the capability of this technique to simultaneously preserve multiple biomarkers in patient samples, the recovered urine samples (with and without ZIF-8 encapsulation, after storage at 40° C. for 1 week) from Patient #3 were assayed by a multiplexed analysis tool, a protein microarray (FIGS. 11D and 11E). FIG. 11D shows fluorescence intensity maps (generated from protein microarray) of #3 patient's urinary biomarkers with and without ZIF-8 encapsulation on paper cards stored at 25 or 40° C. for one week. Frozen liquid sample (−20° C.) was used as a reference. POSs represent 3 distinct Positive Control signal intensities (POS1>POS2>POS3). Results are the mean and standard deviation from two parallel dots for each biomarker. The frozen-liquid samples stored at −20° C. were employed as the reference. The results showed that four detectable acute kidney injury biomarkers (albumin, NGAL, cystatin C and Beta-2 microglobulin) were almost fully (>95%) preserved with ZIF-8 encapsulation, whereas samples without ZIF-8 encapsulation exhibited ~40-60% fluorescence signal intensity loss corresponding to these biomarkers. Overall, these results clearly demonstrate the efficacy of ZIF-8 encapsulation in preserving the dried urinary protein biomarkers on paper substrates at high temperatures.

The final urine pH was measured after mixing 500 μl of urine with 250 μl of zinc acetate and 250 μl of 2-methylimidazole

TABLE 2

Patient urine pH after mixing with ZIF-8 precursors.

| | Original urine pH | Zinc acetate | 2-methylimidazole | Final urine pH |
|---|---|---|---|---|
| Patient #1 | 6.1 | 10 mM | 40 mM | 7.5 |
| | 6.1 | 20 mM | 80 mM | 7.6 |
| | 6.1 | 40 mM | 160 mM | 7.6 |
| Patient #2 | 5.6 | 10 mM | 40 mM | 7.4 |
| | 5.6 | 20 mM | 80 mM | 7.5 |
| | 5.6 | 40 mM | 160 mM | 7.5 |
| Patient #3 | 6.3 | 10 mM | 40 mM | 7.7 |
| | 6.3 | 20 mM | 80 mM | 7.8 |
| | 6.3 | 40 mM | 160 mM | 7.8 |

Example 5: Preservation of Blood and Blood Components

Figure 16:
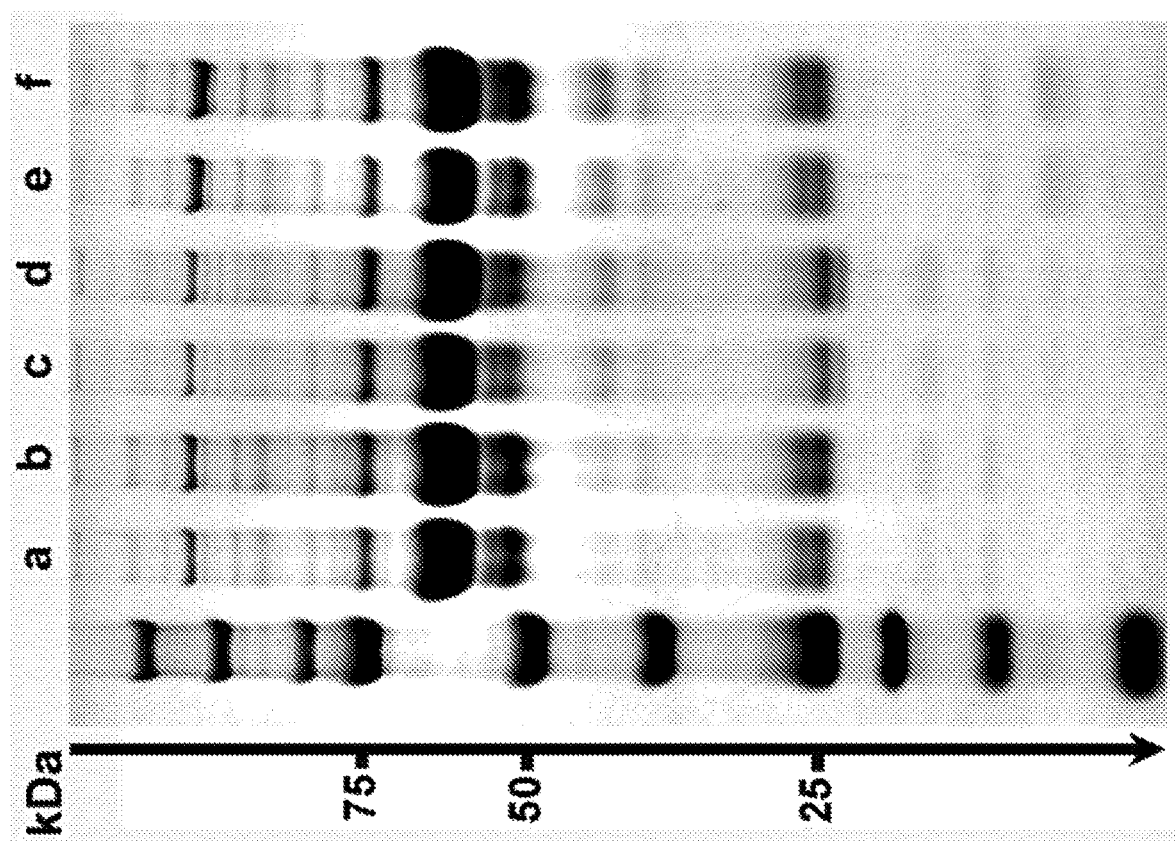
FIG. 16 depicts an exemplary embodiment of SDS-PAGE of serum eluate with (lanes a, c and e) and without (lanes b, d and f) ZIF-8 encapsulation dried on paper substrates in accordance with the present disclosure.
Figure 17:
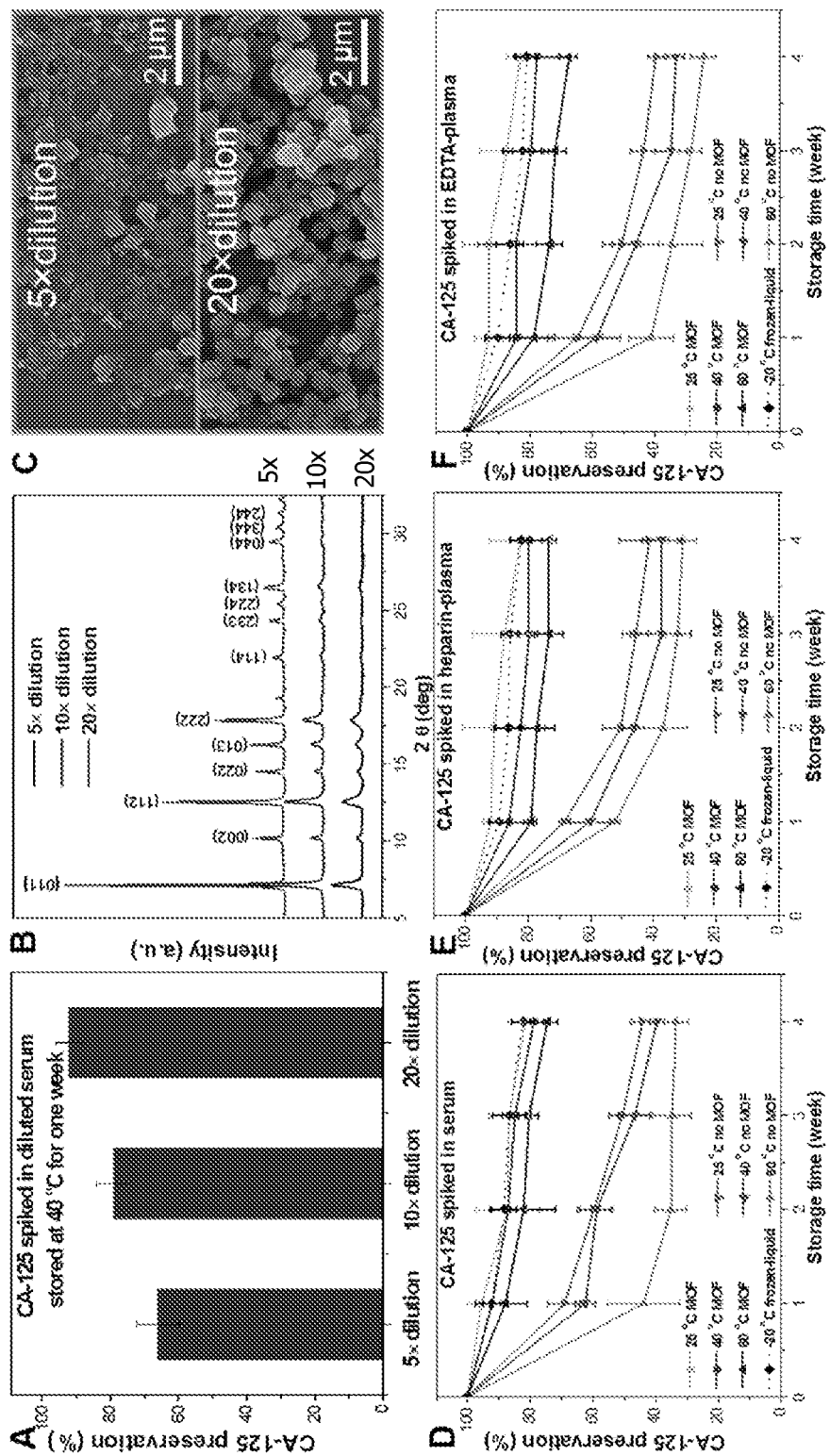
FIG. 17A depicts an exemplary embodiment of preservation efficacy of CA-125 spiked in serum with different dilutions in accordance with the present disclosure.
FIG. 17B depicts an exemplary embodiment of XRD patterns of ZIF-8 crystals formed in the serum with different dilutions in accordance with the present disclosure.
FIG. 17C depicts an exemplary embodiment of SEM images of ZIF-8 crystals formed in 5- and 20-fold diluted serum in accordance with the present disclosure.
FIG. 17D-F depicts exemplary embodiments of preservation efficacy of CA-125 spiked in serum, heparin-plasma or EDTA-plasma on paper card in accordance with the present disclosure.
Figure 18:
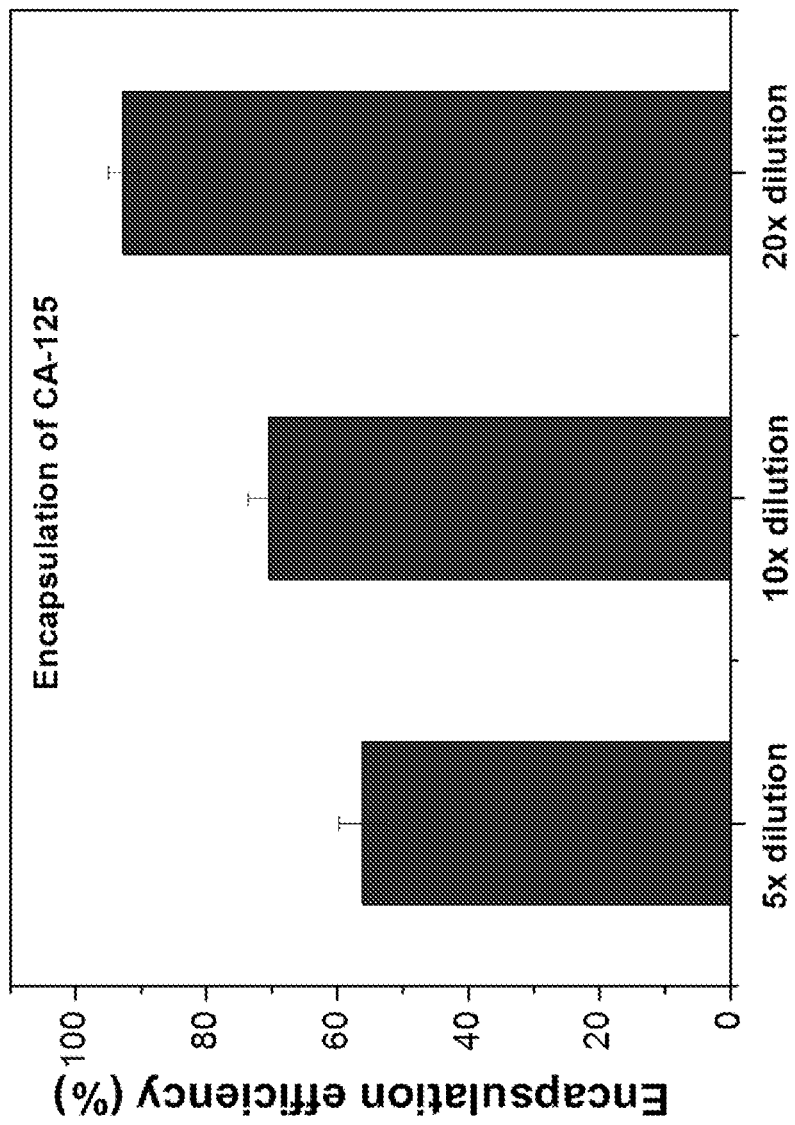
FIG. 18 depicts an exemplary embodiment of encapsulation efficiency of CA-125 (50 µg/ml) spiked in 5-, 10- or 20-fold diluted serum using ZIF-8 encapsulation in accordance with the present disclosure.

Further attention was given to blood (and components serum and plasma), the most common biospecimens in biological and clinical studies. Compared to urine, serum or plasma represents a more complex biological matrix due to the presence of large amount of various proteins such as albumin, globulins and fibrinogen. Before proceeding to assess the preservation of specific protein biomarker, it was confirmed that different types of proteins are extracted from the paper substrates containing dried serum with or without ZIF-8 encapsulation using sodium dodecyl sulfate-polyacrylamide gel electrophoresis (SDS-PAGE), indicating the potential of this technique in preserving multiple protein biomarkers simultaneously in serum or plasma (FIG. 16). FIG. 16 shows SDS-PAGE of the eluate of three healthy volunteers' serum (after 20×dilution) with and without ZIF-8 encapsulation dried on paper substrates (the samples were dried and eluted instantly). Lane a, c and e are corresponding to eluate of volunteer #1, #2 and #3 serum without ZIF-8 encapsulation, respectively. Lane b, d and f are corresponding to eluate of volunteer #1, #2 and #3 serum with ZIF-8 encapsulation, respectively. CA-125, a serum biomarker for ovarian cancer, was used as the model protein and spiked into serum from healthy people. Considering extremely high concentration of serum proteins, the serum was first diluted (5-, 10- or 20-fold) before spiking CA-125 and adding ZIF-8 precursors to ensure ZIF-8 formation and more complete encapsulation. The CA-125 spiked serum samples, both with and without ZIF-8 encapsulation, were dried on paper and stored at 40° C. for 1 week. The results indicated that CA-125 spiked in 20-fold diluted serum afforded the highest preservation (~90%, FIG. 17; storage condition: 40° C. for one week). The poor preservation of CA-125 from 5- and 10-fold diluted serum was due to the incomplete ZIF-8 formation and encapsulation (FIG. 18). The encapsulation efficiency was calculated by subtracting the remaining CA-125 amount in the supernatant after encapsulation and centrifugation (concentration measured by ELISA) from the total CA-125 amount. Results are the mean and standard deviation from three independent experiments. This was further confirmed by XRD and SEM imaging (FIGS. 17B and 17C), revealing decreased ZIF-8 crystal formation with increased total protein concentration in serum. Subsequently, CA-125 was spiked into three different matrices that represent typical blood-derived biospecimens (serum, heparin-anticoagulated plasma and EDTA-anticoagulated plasma from healthy people with 20-fold dilution), dried on paper substrates with and without ZIF-8 encapsulation, and subsequently stored at 25, 40, or 60° C. for different durations of time. CA-125 concentration in the eluate was quantified using sandwich ELISA. In all three matrices, CA-125 with ZIF-8 encapsulation exhibited ~85% preservation after 4 weeks storage at 25 and 40° C., as well as ~75% at 60° C. (FIG. 17D-F). FIGS. 17D-F show preservation efficacy of CA-125 spiked in serum, heparin-plasma or EDTA-plasma on paper card at 25, 40 or 60° C. for different durations. Results are the mean and standard deviation from three independent samples. Within four weeks, the ZIF-8 encapsulation shows comparable preservation, after storage at 25 and 40° C., to the refrigeration method (freezing liquid samples at −20° C.). On the other hand, CA-125 without ZIF-8 encapsulation stored at these three temperatures for 4 weeks displayed ~50%, 40% and 30% preservation, respectively. Remarkably, the preservation efficacy of ZIF-8 encapsulated CA-125 over 4 weeks of storage at 25 and 40° C. was comparable to the refrigeration method (freezing liquid samples at −20° C.) for the same storage duration.

Figure 19:
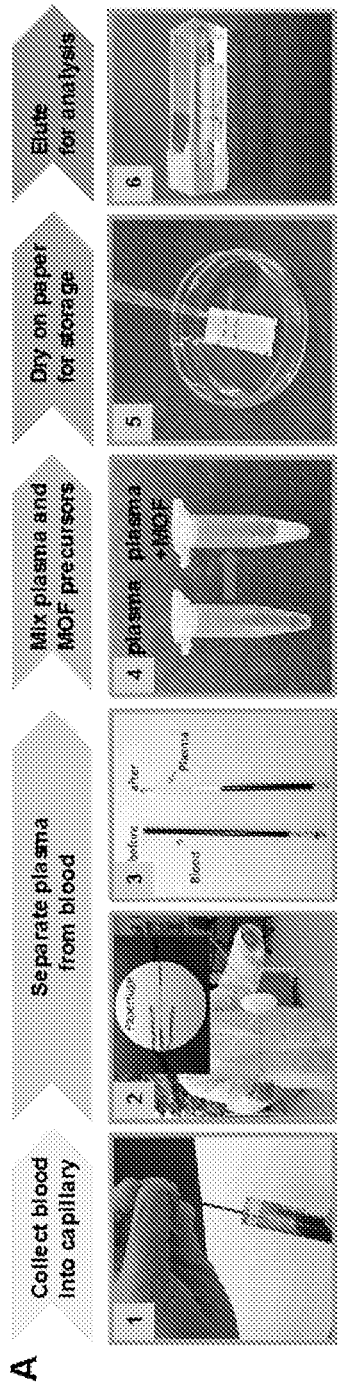
FIG. 19A depicts an exemplary embodiment of a procedure of preserving protein biomarkers in fresh blood samples by combining hand-powered centrifuge ("paperfuge") and MOF-based preservation in accordance with the present disclosure.
FIG. 19B depicts an exemplary embodiment of preservation efficacy of CA-125 spiked in blood under temperature fluctuations in lab in accordance with the present disclosure.
FIG. 19C depicts an exemplary embodiment of preservation efficacy of CA-125 spiked in blood after 10 days of unknown shipping and handling conditions in accordance with the present disclosure.
Figure 19:
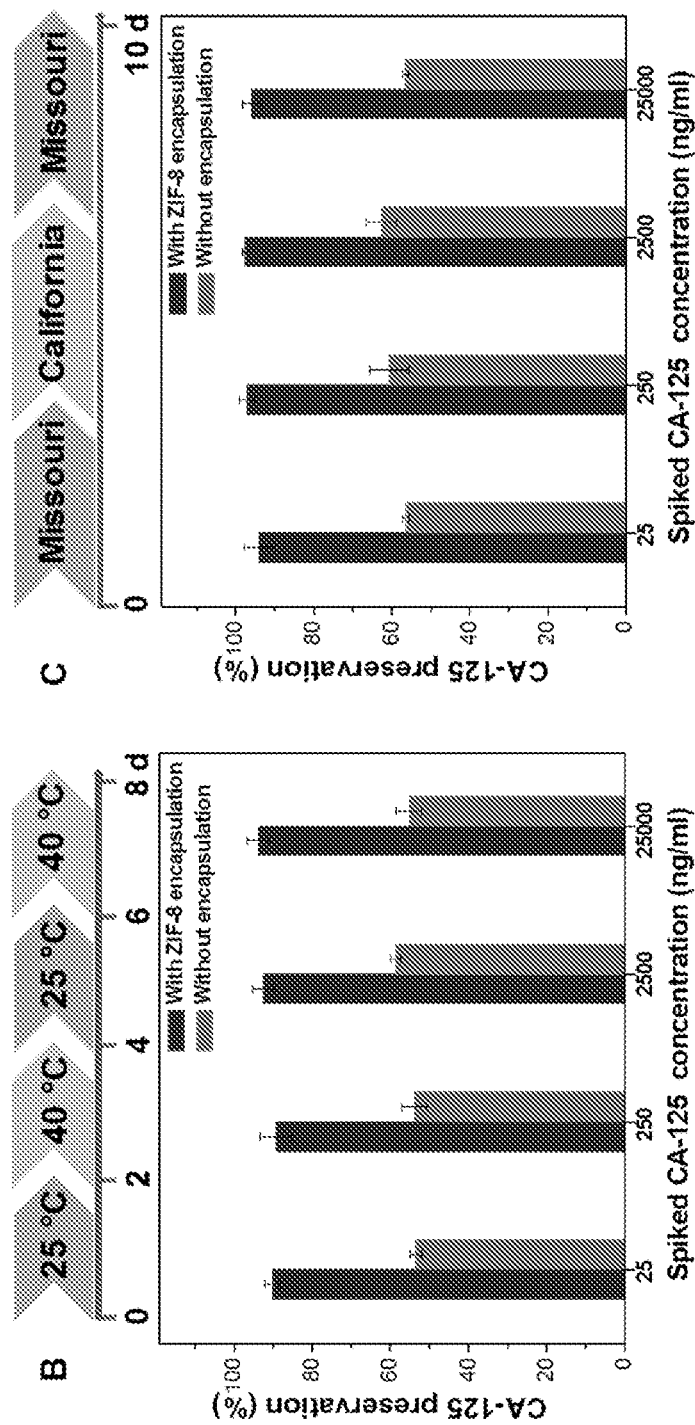

The applicability of this technique was assessed to preserve blood samples drawn in resource-limited settings. Unlike serum and plasma, in some embodiments the presence of a large quantity of whole cells (red and white blood cells and platelets) in blood affects ZIF-8 encapsulation of target protein biomarkers. Considering that in some embodiments ZIF-8 also forms a thick layer on cell surfaces56 and lead to incomplete encapsulation or preservation of target protein biomarkers, it is important to remove blood cells through centrifugation before ZIF-8 encapsulation of protein biomarkers. Unfortunately, centrifuge is typically inaccessible in resource-limited settings considering that conventional systems are bulky, expensive and electrically-powered. A hand-powered centrifuge was implemented that was able to separate plasma from whole blood within 10 minutes for subsequent ZIF-8 encapsulation (FIG. 19A). In order to mimic fresh whole blood samples from ovarian cancer patients, four different concentrations of CA-125 within pathological-relevant range from 25 ng/ml-25 µg/ml were spiked into fresh blood from healthy volunteers.58-59 Then the plasma samples (heparin-anticoagulated) were separated from blood and diluted 20-fold for ZIF-8 encapsulation. To assess the preservation efficacy of this approach under unregulated conditions, two sets of experiments were devised. First, the ZIF-8 preserved plasma samples with the four different CA-125 concentrations were subjected to temperature fluctuations for 8 days (two days 25° C. followed by two days 40° C. as one cycle and run for two cycles, FIG. 19B). Second, the ZIF-8 preserved plasma samples with the four different CA-125 concentrations were shipped to California, USA and sent back to Missouri, USA via a regular shipping package (10 days in unknown shipping and handling conditions, FIG. 19C; results are the mean and standard deviation from three independent samples). Unencapsulated samples dried on papers were used as negative controls in both cases. As shown in FIGS. 19B and 19C, in some embodiments samples with ZIF-8 encapsulation achieve up to 90% of preservation, as opposed to ~50-60% of preservation from control samples. It is also important to note that the preservation efficacy did not significantly change with the variation of CA-125 concentrations. Overall, the experiments here clearly demonstrate the feasibility and robustness of this approach in preserving protein biomarkers in blood samples. By combining with the hand-powered centrifuge, it is possible to directly collect and preserve fresh blood samples in resource-limited settings.

Example 6: Encapsulation of Insulin

Figure 20:
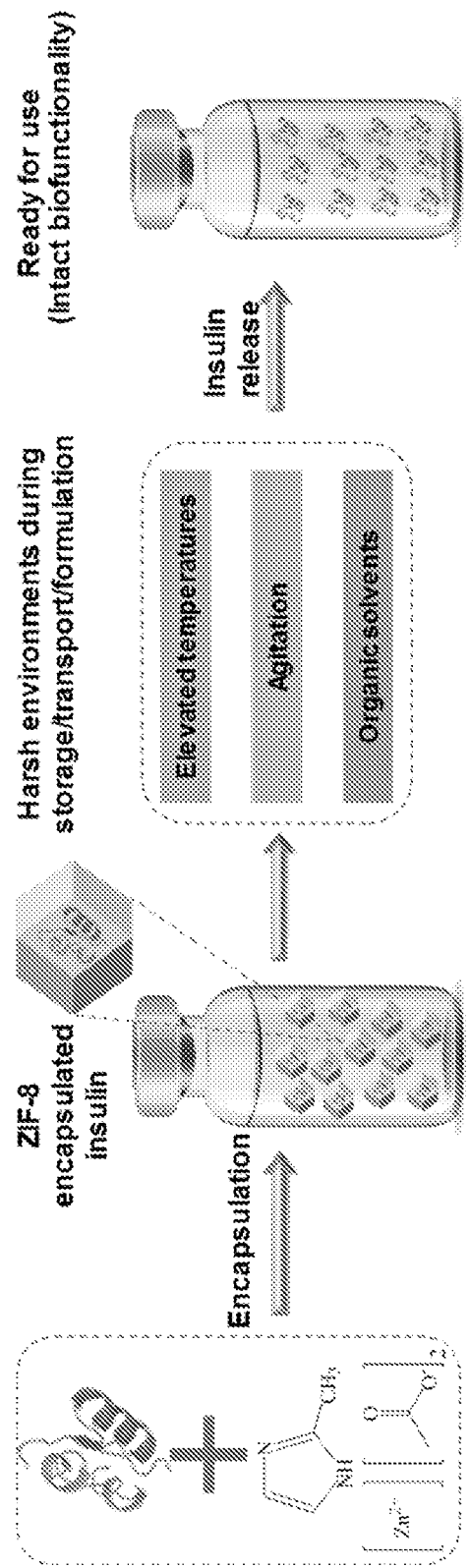
FIG. 20 depicts an exemplary embodiment of a schematic illustration of ZIF-8 encapsulation for preserving insulin structure and bioactivity against various environmental stressors in accordance with the present disclosure.
Figure 21:
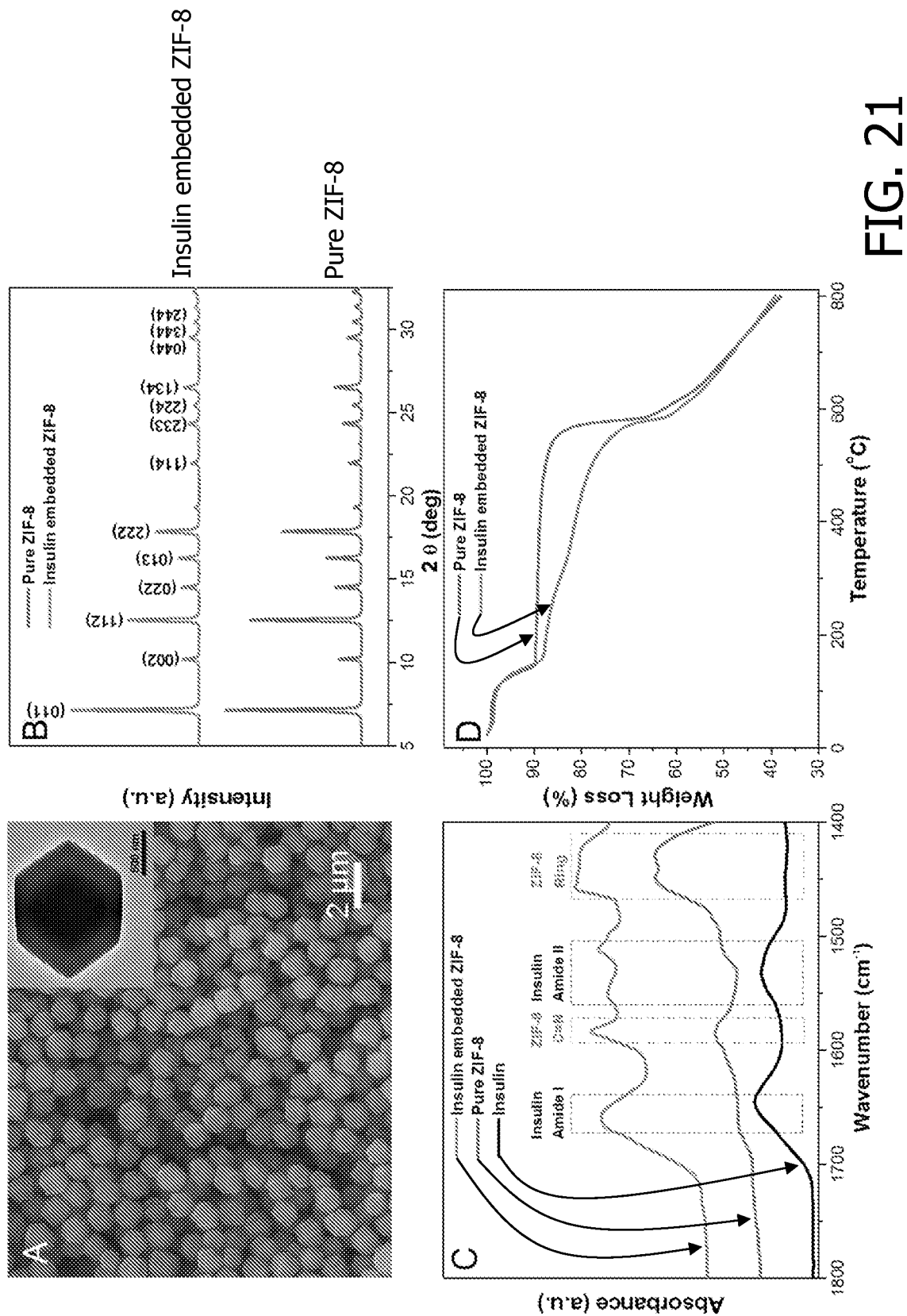
FIG. 21A depicts an exemplary embodiment of scanning electron microscope image of insulin-embedded ZIF-8 in accordance with the present disclosure.
FIG. 21B depicts an exemplary embodiment of powder X-ray diffraction spectra of insulin-embedded ZIF-8 and pure ZIF-8 in accordance with the present disclosure.
FIG. 21C depicts an exemplary embodiment of Fourier transform infrared spectra of insulin-embedded ZIF-8, pure ZIF-8 and pure insulin in accordance with the present disclosure.
FIG. 21D depicts an exemplary embodiment of thermogravimetric analysis of insulin-embedded ZIF-8 and pure ZIF-8 in accordance with the present disclosure.
Figure 22:
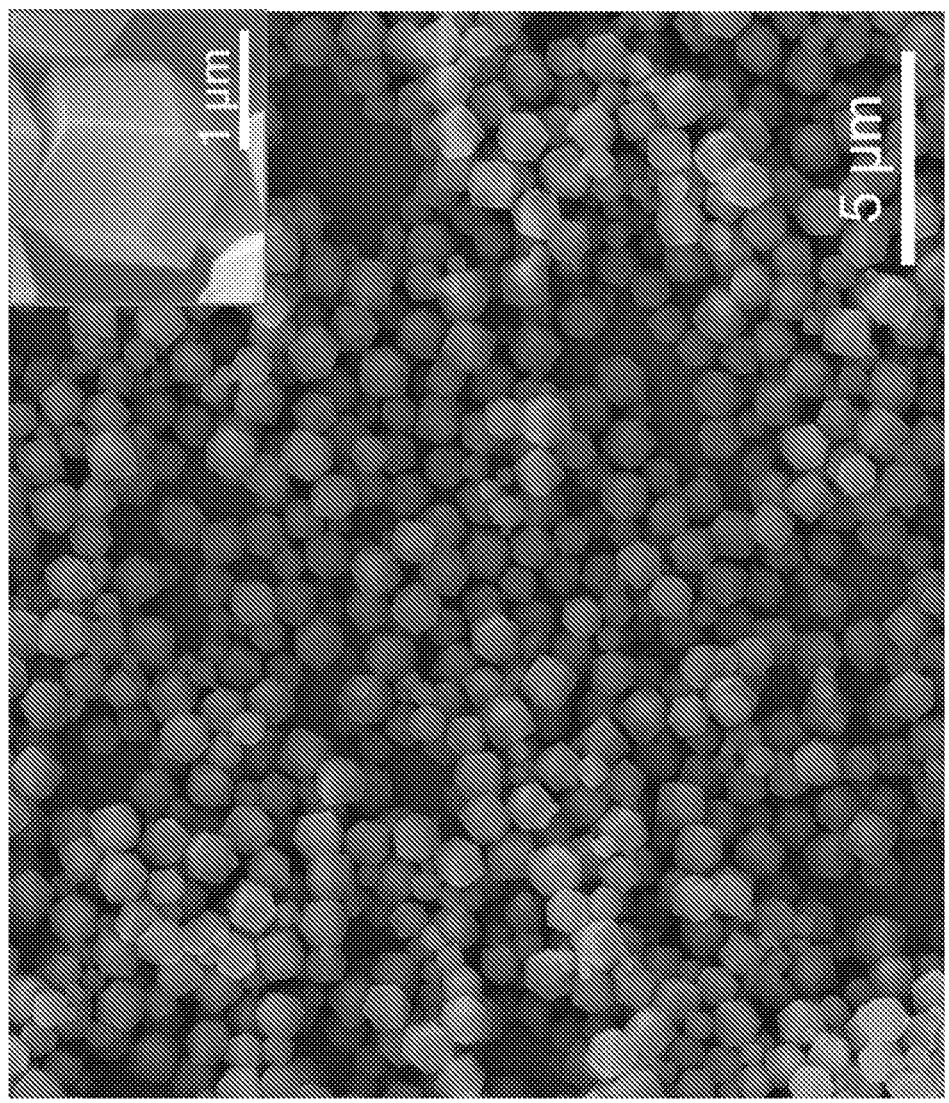
FIG. 22 depicts an exemplary embodiment of scanning electron microscope images of pure ZIF-8 in accordance with the present disclosure.
Figure 23:
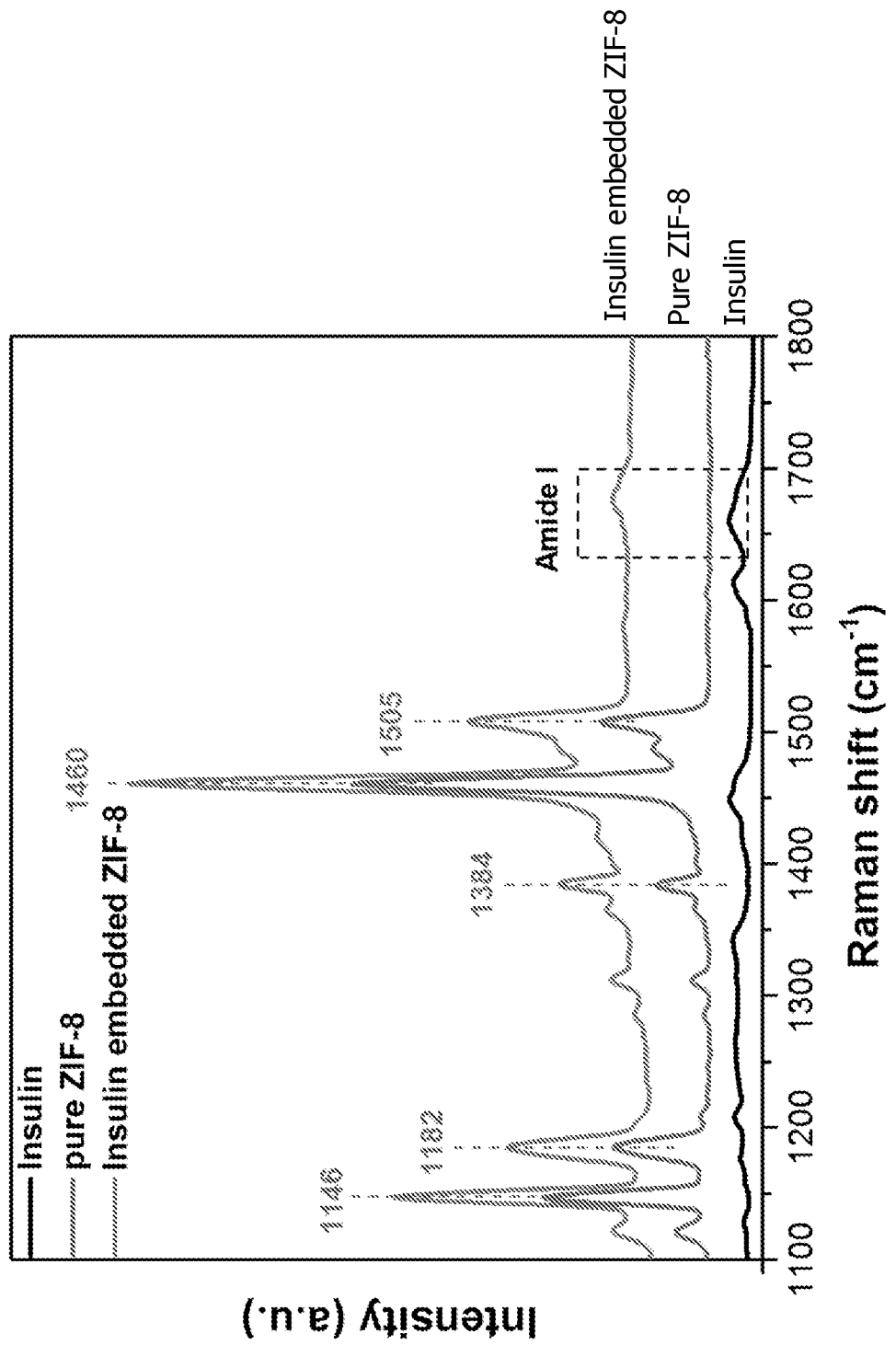
FIG. 23 depicts an exemplary embodiment of Raman spectra of insulin-embedded ZIF-8, pure ZIF-8 and pure insulin in accordance with the present disclosure.

As a member of zeolitic imidazolate framework family of MOFs, ZIF-8 offers high thermal and hydrothermal stabilities, and has been demonstrated to be a nontoxic and biocompatible material for drug delivery. Here, the encapsulation of insulin into ZIF-8 crystals is achieved under mild aqueous conditions by mixing insulin solution with aqueous solutions of 2-methylimidazole and zinc acetate (FIG. 20). The suspension of insulin-embedded ZIF-8 was subjected to elevated temperatures, agitation and organic solvent. In some embodiments, the preserved insulin is released from ZIF-8 crystals within 1 minute, enabling on-demand usage, thus extending the benefits of advanced protein therapeutics in resource-limited settings. After 12 h incubation, insulin-embedded ZIF-8 crystals were formed and could be easily collected by centrifugation. Scanning electron microscope and transmission electron microscope images showed that insulin-embedded ZIF-8 crystals exhibited a uniform size of ~1 µm (FIG. 21; Inset: Transmission electron microscope image of insulin-embedded ZIF-8). The typical rhombic dodecahedral shape of the crystals (inset of FIG. 21A) was similar to that of the pure ZIF-8 crystals (FIG. 22). The powder X-ray diffraction (XRD) pattern of insulin-embedded ZIF-8 crystals also exhibited all the typical peaks of pure ZIF-8 (FIG. 21B). To further ascertain the formation of ZIF-8 crystals and the encapsulation of insulin, Fourier transform infrared spectroscopy (FTIR) and Raman spectroscopy were employed. The FTIR spectrum obtained from pure insulin exhibited absorption peaks at 1640-1670 and 1510-1560 cm$^{-1}$, corresponding to amide I and amide II bands of insulin, respectively (FIG. 21C, black spectrum). Following ZIF-8 encapsulation, the FTIR spectrum (orange spectrum) revealed absorption bands associated with ZIF-8 crystals at 1584 cm$^{-1}$ corresponding to the C=N stretching of imidazole and at 1400-1500 cm$^{-1}$ corresponding to the imidazole ring stretching in addition to the amide I and amide II bands of insulin. FIG. 21D shows thermogravimetric analysis of insulin-embedded ZIF-8 and pure ZIF-8. Similar results were observed by Raman spectroscopy, which also indicated the presence of insulin in ZIF-8 crystals (FIG. 23). The Raman spectrum obtained from pure insulin exhibits a broad band at 1630-1690 cm$^{-1}$, corresponding to amide I band of protein. After encapsulation by ZIF-8, the amide I band of encapsulated insulin is still present (and not present in pure ZIF-8), while characteristic peaks of 2-methylimidazole are observed at 1146, 1182, 1384, 1460 and 1505 cm$^{-1}$ corresponding to C—N stretching, C—N stretching plus N—H wagging, CH$_3$ bending, C—H wagging and C—N stretching plus N—H wagging, respectively.

Example 7: Encapsulation Efficiency Quantification

Figure 24:
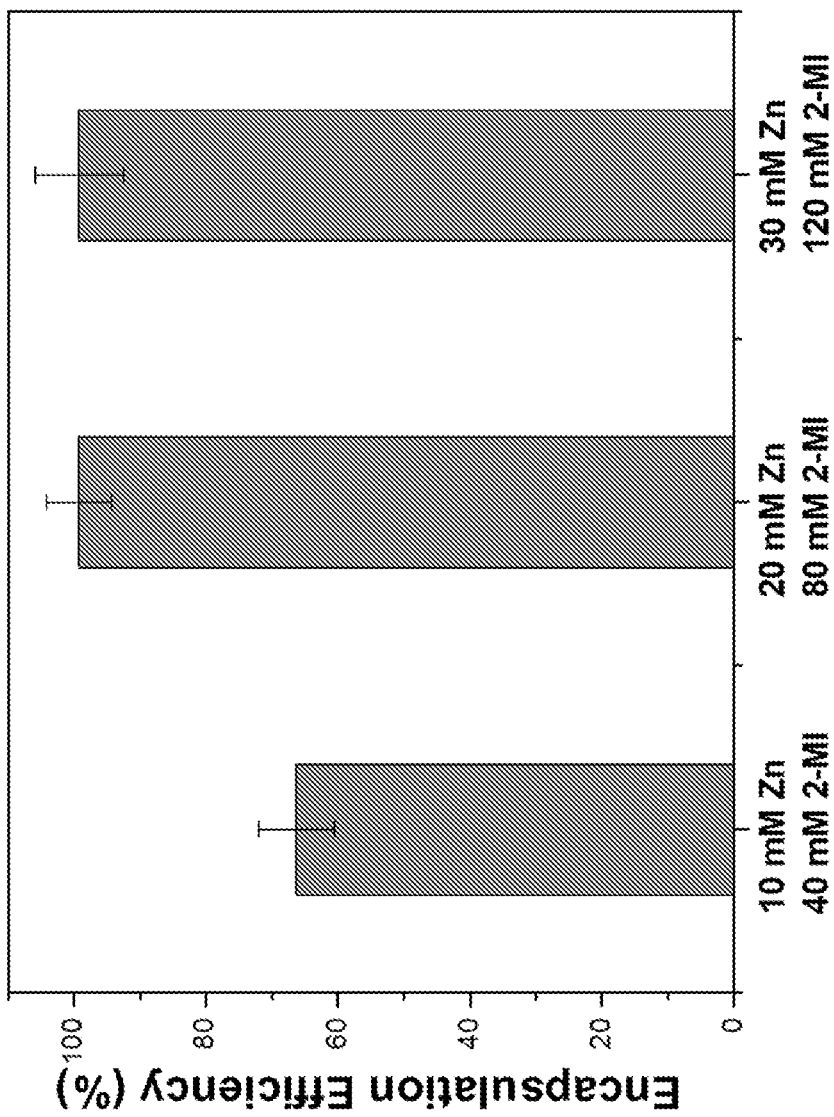
FIG. 24 depicts an exemplary embodiment of encapsulation efficiency of insulin (0.6 mg/ml) using three different concentrations of ZIF-8 precursors in accordance with the present disclosure.

To quantify the encapsulation efficiency, residual insulin concentration in the supernatant after crystal formation and removal by centrifugation was determined by sandwich enzyme-linked immunosorbent assay (ELISA). It was found that the encapsulation efficiency was dependent on the concentration of ZIF-8 precursors. Specifically, when the concentrations of zinc acetate and 2-methylimidazole were set to 20 mM and 80 mM, respectively, almost 100% of insulin (0.6 mg/mL) was encapsulated within ZIF-8 crystals (FIG. 24). The encapsulation efficiency was calculated by subtracting the residual insulin amount in the supernatant after crystal formation and removal by centrifugation from the total insulin amount. Insulin concentration was measured by ELISA. Results are the mean and standard deviation from three independent experiments. In a control experiment, encapsulation efficiency was extremely low (~5%, owing to physical adsorption) for simply mixing the insulin solution with pre-synthesized pure ZIF-8 crystals (not shown). This physical mixing of pre-synthesized ZIF-8 crystals with insulin was in stark contrast with the protein-encapsulating approach (i.e., formation of ZIF-8 crystals in the presence of insulin), which exhibited high encapsulation efficiency (~100%). With nearly complete encapsulation, the loading amount of insulin in the biocomposite was determined using thermogravimetric analysis (TGA). The mass loss profile of insulin-loaded ZIF-8 was significantly different compared to that of the pure ZIF-8. The first weight loss at ~100° C. in both pure and insulin-loaded ZIF-8 crystals (~10% weight loss) corresponds to the removal of guest molecules (mainly H$_2$O) from the cavities and some unreacted reagents. As opposed to pure ZIF-8, insulin-loaded ZIF-8 crystals exhibited a ~10% weight loss between 200° C. to 400° C., which is attributed to the decomposition of insulin (FIG. 21D). Taken together, these results indicate that insulin is encapsulated with ZIF-8 crystals with a high encapsulation efficiency.

Example 8: Efficacy of ZIF-8 Encapsulation for Preserving Insulin

Figure 25:
FIG. 25 depicts an exemplary embodiment of images of free insulin in solution, insulin with ZIF-8 encapsulation and released insulin from ZIF-8 encapsulation after adding EDTA to break ZIF-8 crystals in accordance with the present disclosure.
Figure 26:
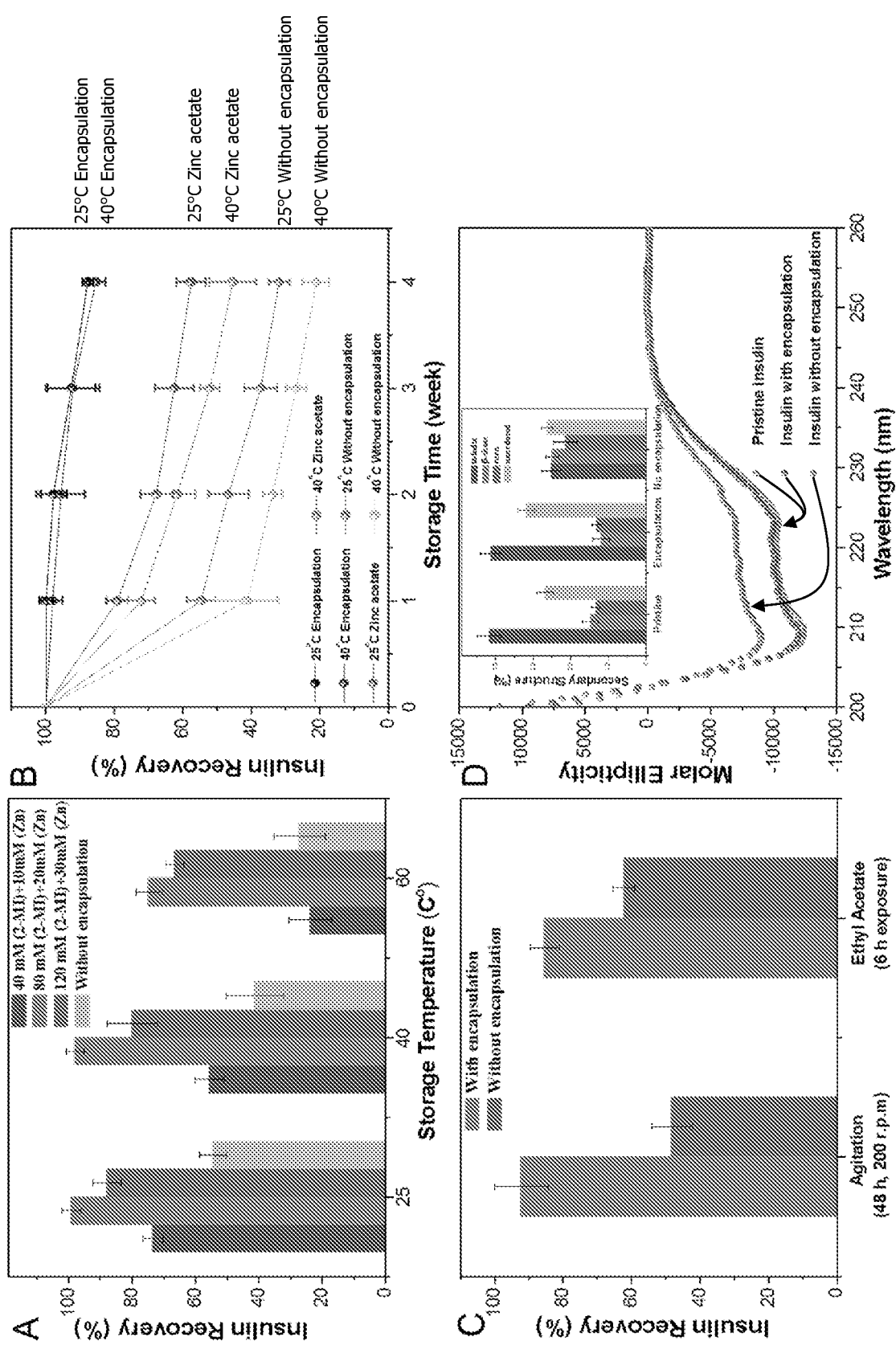
FIG. 26A depicts an exemplary embodiment of recovery percentage of insulin with ZIF-8 (three different precursor concentrations) or without ZIF-8 encapsulation after 1 week incubation at 25, 40 or 60° C. in accordance with the present disclosure.
FIG. 26B depicts an exemplary embodiment of recovery percentage of insulin with ZIF-8 encapsulation, with addition of zinc ion or without ZIF-8 encapsulation incubated at 25, 40 or 60° C. for different time durations in accordance with the present disclosure.
FIG. 26C depicts an exemplary embodiment of recovery percentage of insulin with or without ZIF-8 encapsulation after subjecting it to agitation and ethyl acetate at room temperature in accordance with the present disclosure.
FIG. 26D depicts an exemplary embodiment of circular dichroism spectra (CD) in accordance with the present disclosure.
Figure 27:
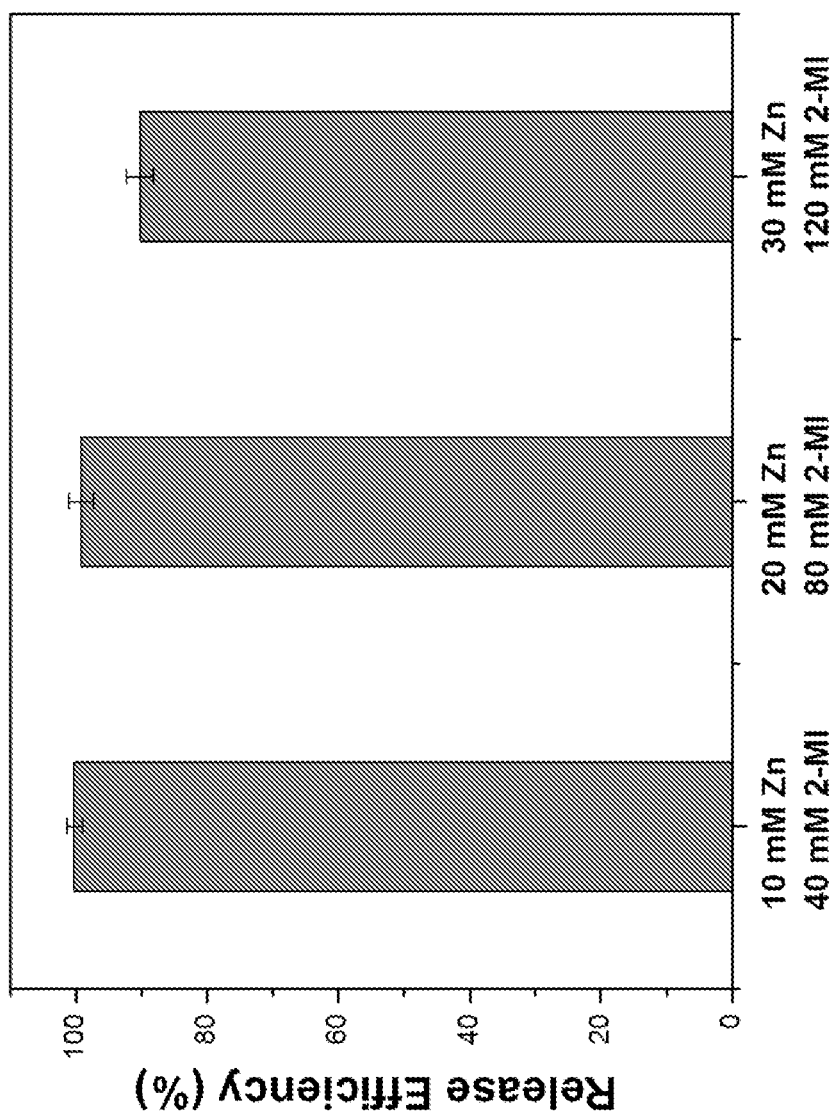
FIG. 27 depicts an exemplary embodiment of release efficiency of insulin from ZIF-8 encapsulation (formed by three different concentrations of precursors) by adding EDTA in accordance with the present disclosure.
Figure 28:
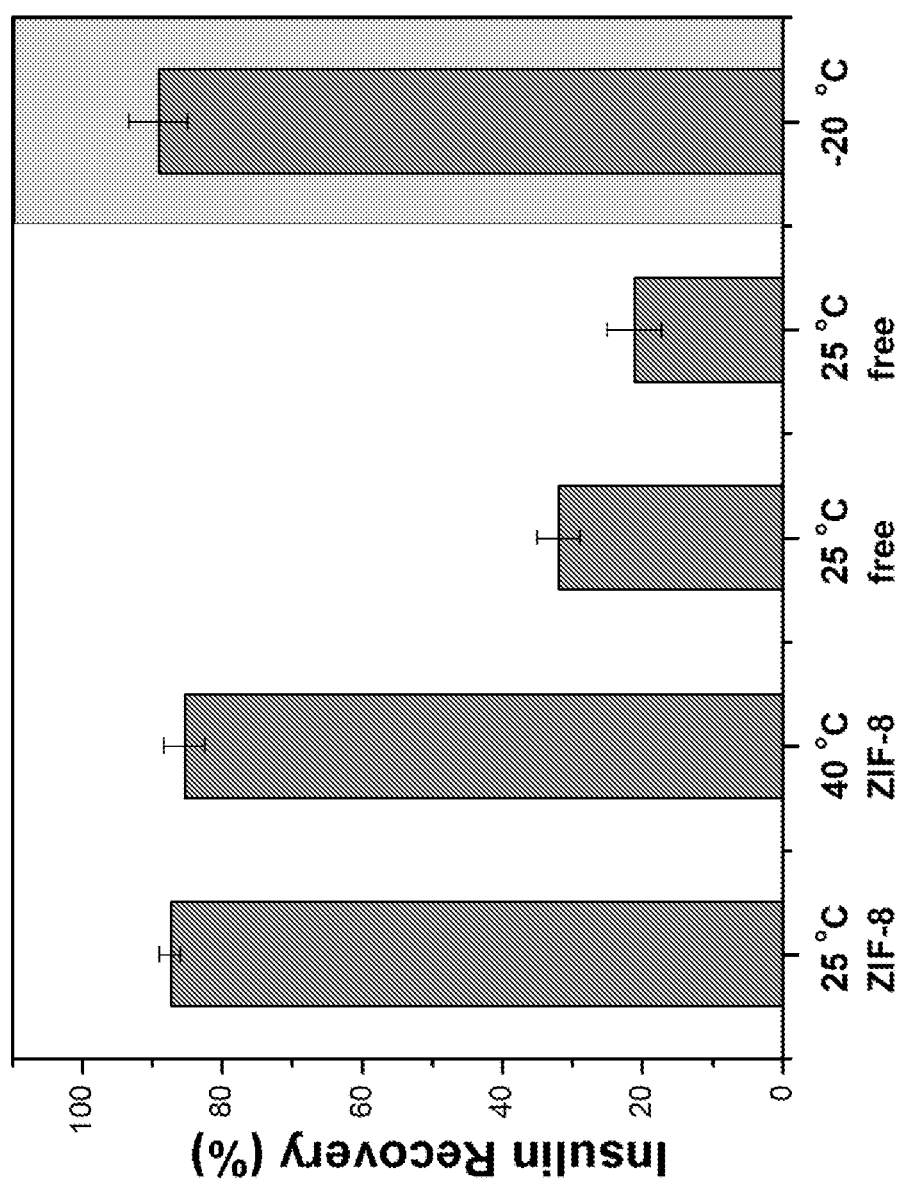
FIG. 28 depicts an exemplary embodiment of recovery percentage of insulin with or without ZIF-8 encapsulation after 4 weeks incubation at 25 or 40° C. in accordance with the present disclosure.

Elevated temperature is the primary detrimental condition during insulin transport and storage, an issue likely to be exacerbated by the increasing epidemic of diabetes in the developing countries, where refrigeration or "cold chain" facilities are not guaranteed. At high temperatures, insulin undergoes both physical (such as unfolding, non-native aggregation and fibrillation) and chemical degradations (such as deamidation, disulfide destruction and reshuffling). To assess the efficacy of ZIF-8 encapsulation in preserving insulin in solution state under non-refrigerated storage conditions, ZIF-8 encapsulated insulin and unencapsulated insulin were stored at 25, 40 or 60° C. for 1 week. After 1 week, the ZIF-8 encapsulated insulin was released by adding ethylenediaminetetraacetic acid (EDTA) to dissociate the ZIF-8 crystals by breaking the coordination bonds between zinc and 2-methylimidazole (FIG. 25). The released insulin and unencapsulated insulin were then quantified by ELISA. The preservation efficacy (insulin recovery %) was calculated by comparing the recovered amount of insulin to the insulin amount prior to incubation. Testing of three different concentrations of ZIF-8 precursors revealed that 20 mM zinc acetate with 80 mM 2-methylimidazole provided the highest preservation efficacy at all three different temperatures (FIG. 26A). Specifically, ZIF-8 encapsulated insulin showed more than 95% recovery after 1 week storage at 25 or 40° C., as well as more than 70% at 60° C. Conversely, unencapsulated insulin stored at these temperatures for 1 week exhibited less than 60%, 50% and 30% recovery at 25, 40 and 60° C., respectively. Compared to the optimal precursor concentrations, the low insulin recovery upon using 10 mM zinc acetate with 40 mM 2-methylimidazole is attributed to the incomplete encapsulation of insulin (FIG. 24). In contrast, higher concentrations (30 mM zinc acetate with 120 mM 2-methylimidazole) of the precursors compared to the optimal concentrations, led to incomplete release of insulin (~90%, FIG. 27) resulting in slightly lower recovery. After mixing insulin solution (0.6 mg/ml, 5 ml) with ZIF-8 precursors (0.5 ml zinc acetate and 0.5 ml 2-methylimidazole, final concentrations after mixing as shown in x-axis) for 12 h to form the crystals, EDTA (1 ml, 120 mM) was added to release the insulin encapsulated within ZIF-8 crystals. In three cases, the solutions became transparent after adding EDTA. The insulin amount in the solution was measured by ELISA and compared with total insulin amount before encapsulation. Results are the mean and standard deviation from three independent experiments. Subsequently, using the optimal ZIF-8 precursor concentrations (20 mM zinc acetate with 80 mM 2-methylimidazole), the storage time was extended at different temperatures up to 4 weeks. Different vials of native or ZIF-8 preserved insulin were sampled at selected time intervals (2, 3 or 4 weeks) to monitor possible changes in the insulin recovery (FIG. 26B). With the ZIF-8 encapsulation, 90% insulin was recovered after storage at 25 or 40° C. up to 4 weeks (the maximum time tested). Significantly, after 4 weeks at 25 or 40° C., insulin with ZIF-8 encapsulation showed comparable recovery to the unencapsulated insulin stored at −20° C. (the current "gold standard" as the control, storage temperature required by the manufacturer) (FIG. 28). The ZIF-8 encapsulated insulin showed comparable recovery, after storage at either room temperature or elevated temperature, to the "gold standard" method (freezing free insulin solution at −20° C.). Zinc acetate alone was also tested for preservation efficacy, considering that zinc ions could also increase the thermal stability of insulin by forming insulin hexamer. However, the preservation efficacy of zinc acetate alone was 30%-40% lower than that of ZIF-8 encapsulation. These results clearly demonstrate the feasibility and superiority of using ZIF-8 encapsulation for preserving insulin in solution at high temperatures.

Example 9: Encapsulation Preservation Against Protein Denaturation by Mechanical Agitation or Organic Solvent Apart from elevated temperatures, therapeutic proteins are often subjected to mechanical agitation during transport and formulation. In the case of insulin, it is known that mechanical agitation can cause partial unfolding and irreversible aggregation that contains high levels of non-native, intermolecular β-sheet structures. Moreover, therapeutic proteins can also be exposed to an aqueous-organic interface during diverse formulation processes such as emulsion or coacervation, which can also be detrimental to the protein structure. The efficacy of ZIF-8 encapsulation was investigated in preserving insulin against mechanical agitation or organic solvent that would normally lead to protein denaturation. To mimic the scenario during transport or formulation, insulin in phosphate-buffered saline (PBS) with and without ZIF-8 encapsulation was vortexed at 200 rpm for 48 h. As shown in FIG. 26C, ZIF-8 encapsulated insulin was recovered over 90%, in contrast to less than 50% recovery from unencapsulated insulin in PBS. In another case, insulin in PBS with and without ZIF-8 encapsulation was first mixed with ethyl acetate, a typical organic solvent used in emulsion processing, and then mechanically agitated for 6 h. The unencapsulated insulin in PBS exhibited less than 60% recovery, whereas ZIF-8 encapsulated insulin was recovered over 80%. The excellent recovery after organic solvent exposure and mechanical agitation is attributed to the tight confinement of the biomacromolecules within ZIF-8 framework, which significantly lowers the free volume available for chain mobility.

Figure 29:
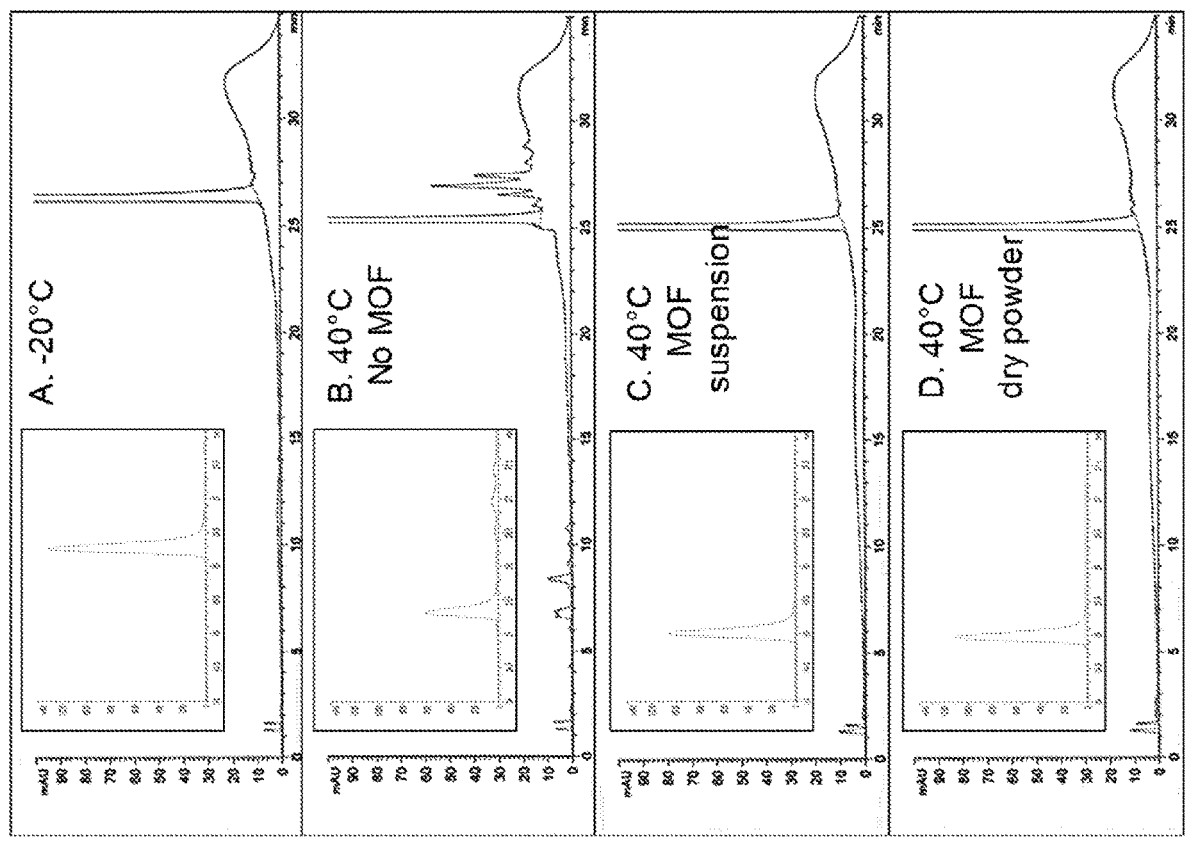
FIG. 29 depicts an exemplary embodiment of high-performance liquid chromatography analysis of (A): insulin stored in solution at −20° C. for 1 week, (B): unencapsulated insulin stored in solution at 40° C. for 1 week, (C) released insulin from ZIF-8 encapsulation stored in suspension at 40° C. for 1 week and (D): released insulin from ZIF-8 encapsulation stored in dry powder at 40° C. for 1 week, in accordance with the present disclosure.
Figure 30:
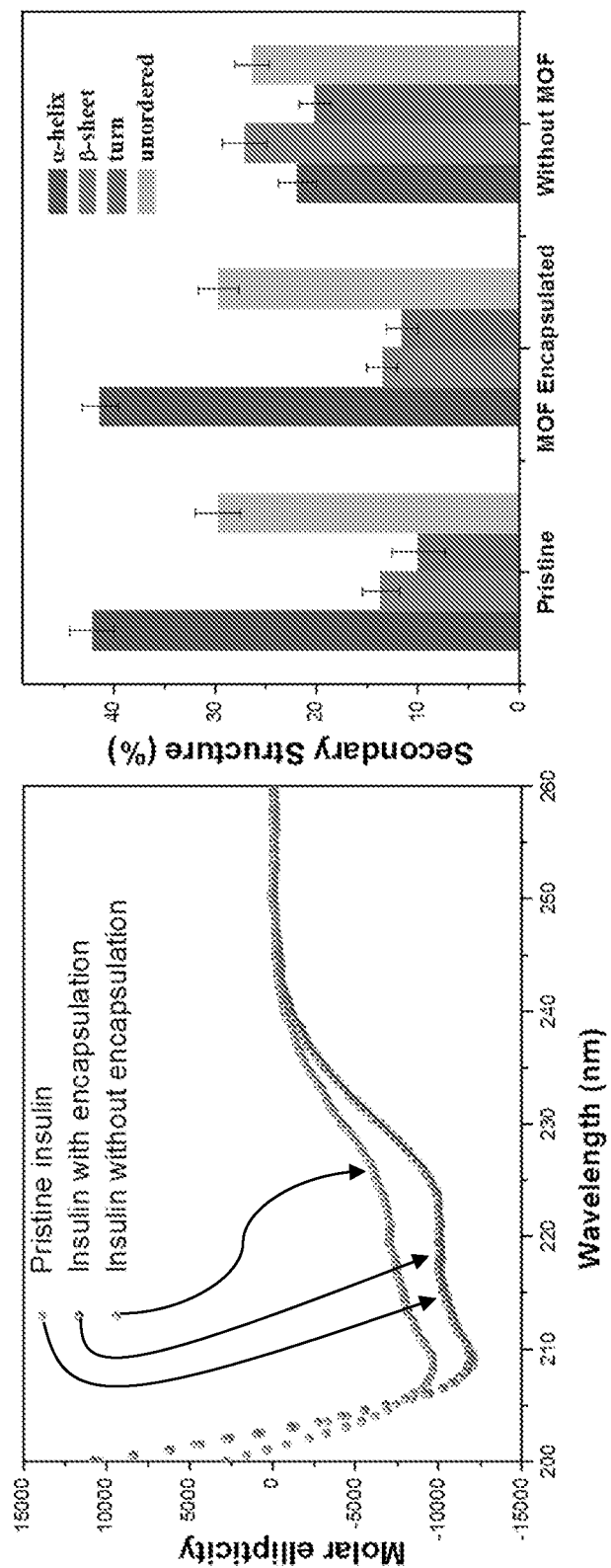
FIG. 30 depicts an exemplary embodiment of CD spectra of insulin after agitation and secondary structures obtained from the CD spectra in accordance with the present disclosure.
Figure 31:
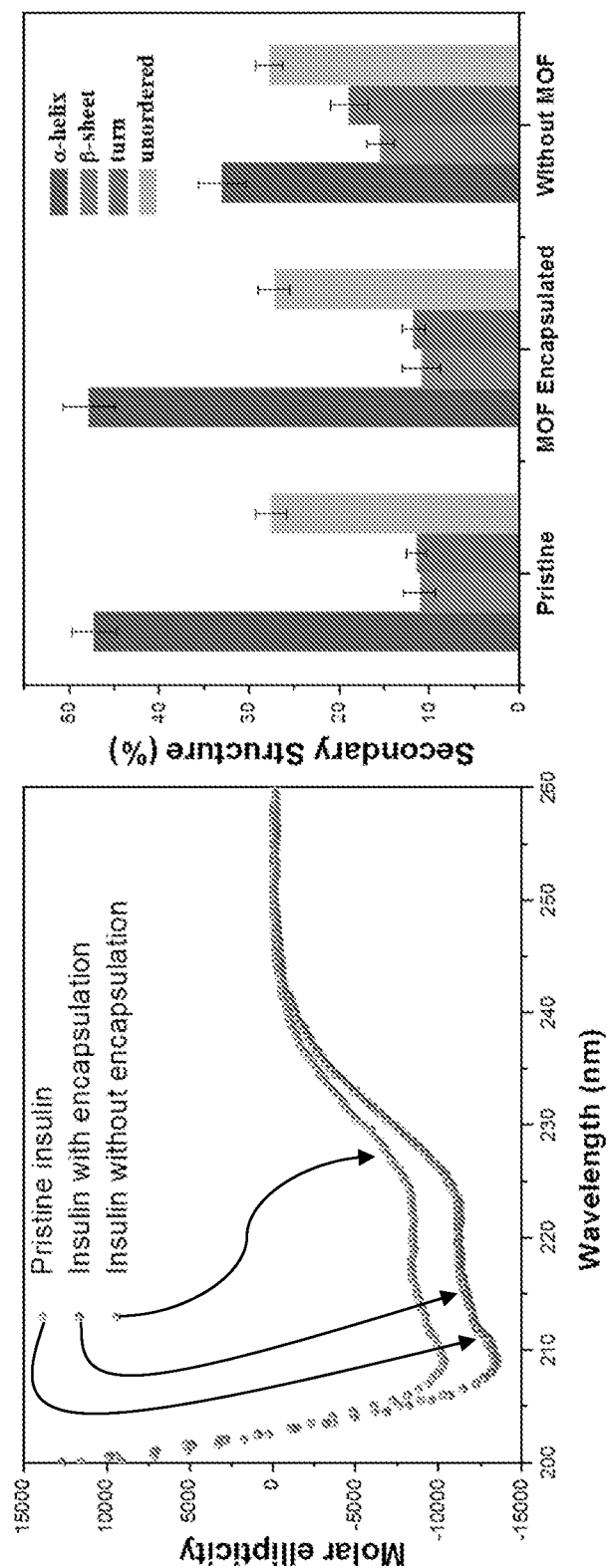
FIG. 31 depicts an exemplary embodiment of CD spectra of insulin after solvent exposure and secondary structures obtained from the CD spectra in accordance with the present disclosure.

To further confirm that ZIF-8 encapsulation preserves the insulin structure, circular dichroism (CD) spectroscopy was employed to characterize the secondary structure of insulin with and without ZIF-8 encapsulation after 1 week incubation at 40° C. (FIG. 26D). FIG. 26D shows circular dichroism spectra of pristine insulin prior to incubation, released insulin from ZIF-8 encapsulation after 1 week incubation at 40° C. and insulin without ZIF-8 encapsulation after 1 week incubation at 40° C. Inset: Secondary structure content of the three types of insulin obtained from the CD spectra. Results are the mean and standard deviation from three independent samples. As expected, elevated temperature caused a significant change (an increase in the β-sheet content along with the decrease in the α-helical content) of the secondary structure of unencapsulated insulin in PBS, as shown in the CD spectrum. In contrast, the secondary structure of ZIF-8 encapsulated insulin was found to be very similar to that of the pristine insulin, indicating that ZIF-8 encapsulation is able to maintain the structure of insulin. In addition to CD spectroscopy, high-performance liquid chromatography (HPLC) also demonstrated the preserved insulin structure by the ZIF-8 encapsulation (FIG. 29; Inset: zoom-in peak at ~25 min). Similar results were observed upon subjecting the encapsulated and unencapsulated insulin to mechanical agitation and organic solvent exposure (FIGS. 30 and 31). FIG. 30 discloses the following: Left: CD spectra of pristine insulin prior to agitation, released insulin from ZIF-8 encapsulation after 48 h agitation at 200 rpm and insulin without ZIF-8 encapsulation after 48 h agitation at 200 rpm; Right: secondary structure content of the three types of insulin obtained from the CD spectra. The results are the mean and standard deviation from three independent samples. FIG. 31 discloses the following: Left: CD spectra of pristine insulin prior to exposure to ethyl acetate, released insulin from ZIF-8 encapsulation after exposure to ethyl acetate for 6 h and insulin without ZIF-8 encapsulation after exposure to ethyl acetate for 6 h; and, right: secondary structure content of the three types of insulin obtained from the CD spectra. Results are the mean and standard deviation from three independent samples. Notably, mechanical agitation converted the unencapsulated insulin from an overall rich helical to dominant β-sheet structure, which indicates severe aggregation of the protein. Overall, CD spectroscopy and HPLC provide direct evidence for the preservation of the insulin structure with ZIF-8 encapsulation.

Figure 32:
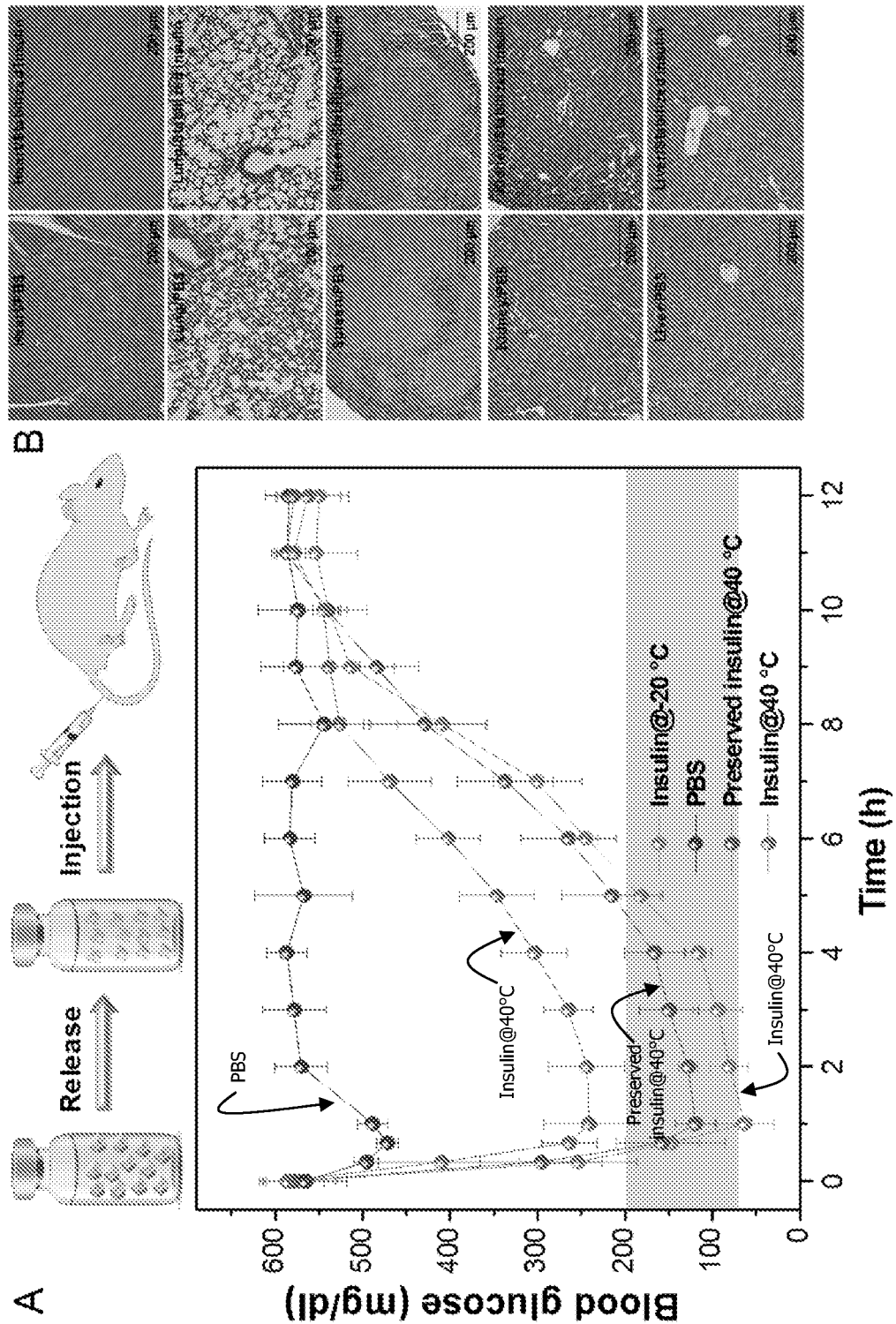
FIG. 32A depicts an exemplary embodiment of (A) In vivo studies of insulin preservation efficacy of ZIF-8 encapsulation in accordance with the present disclosure.
FIG. 32B depicts an exemplary embodiment of histology study to assess toxicity in accordance with the present disclosure.

Example 10: In Vivo Study Using Streptozotocin (STZ)-Induced Type 1 Diabetic Mice After establishing the chemical stability and structural integrity of ZIF-8 encapsulated insulin, the biological activity of ZIF-8 encapsulated insulin was assessed by measuring the effectiveness of ZIF-8 encapsulated insulin for treating hyperglycemia in streptozotocin-induced type 1 diabetic mice. The mice were randomly divided to four groups and intravenously injected with PBS solution, insulin stored at −20° C., ZIF-8 encapsulated insulin or unencapsulated insulin stored at 40° C. for 1 week, respectively. The ZIF-8 encapsulated insulin was released by adding EDTA before injection. The blood glucose concentrations of mice in each group were then monitored for 12 h. As shown in FIG. 32A and FIG. 32B, for mice treated with insulin stored at −20° C. and with ZIF-8 encapsulated insulin stored at 40° C., the blood glucose levels comparably and rapidly decreased to normoglycemic (70-200 mg/dL) within 1 h, were maintained in the normoglycemic range for 4 h, and then increased to hyperglycemic range (~550 mg/dL) within 12 h. Histological evaluation of the major organs of the mice at 5 days after intravenous injection of PBS or stabilized insulin. No symptoms of inflammation and/or lesion were observed in the hematoxylin and eosin stained images. Blood glucose concentrations in streptozotocin-induced diabetic mice after administration of PBS solution, insulin stored at −20° C. for 1 week, ZIF-8 encapsulated insulin and unencapsulated insulin stored at 40° C. for 1 week. The ZIF-8 encapsulated insulin was released by adding EDTA before injection. Results are the mean±standard deviation (n=3). This unequivocally indicated the comparable bioactivity of ZIF-8 encapsulated insulin to the refrigerated equivalence. In contrast, insulin without ZIF-8 encapsulation and storage at 40° C. only moderately decreased glucose concentrations. The partial loss of insulin bioactivity here could be attributed to the loss of structure integrity of insulin at elevated temperatures as confirmed by the aforementioned ELISA, CD and HPLC experiments. Overall, the in vivo experiments clearly demonstrate the excellently preserved bioactivity of insulin through ZIF-8 encapsulation.

STZ-induced male C57BL/6 (6-10 weeks) type 1 diabetic mice were purchased from Jackson Laboratory (USA). The blood glucose levels of mice were tested 1 day before administration by collecting blood (~3 μL) from the tail vein and measuring using the Clarity GL2Plus glucose monitor (VWR, USA). The mice were randomly divided into four groups (3 mice each group) and intravenously injected via lateral tail vein with PBS solution, insulin stored at −20° C., ZIF-8 preserved insulin (dissociated by EDTA) and insulin alone stored at 40° C. for 1 week, respectively. The insulin dose for each mouse was 1 mg/kg (125 μg/mL, ~200 μL).

The blood glucose level was measured from tail vein blood samples (~3 μL) of mice at different time points (at 10, 20, 40, and 60 min, and once per hour afterward for the first 12 h in the day of administration). Mice were anesthetized with 2% isoflurane. The mice treated with ZIF-8 preserved insulin and PBS were sacrificed after 5 days administration, and major organs were collected and sliced for haematoxylin and eosin (H&E) staining.

Example 11: In Vitro Study Using Mouse Embryonic Fibroblast (Cell Line: 3T3)

Figure 33:
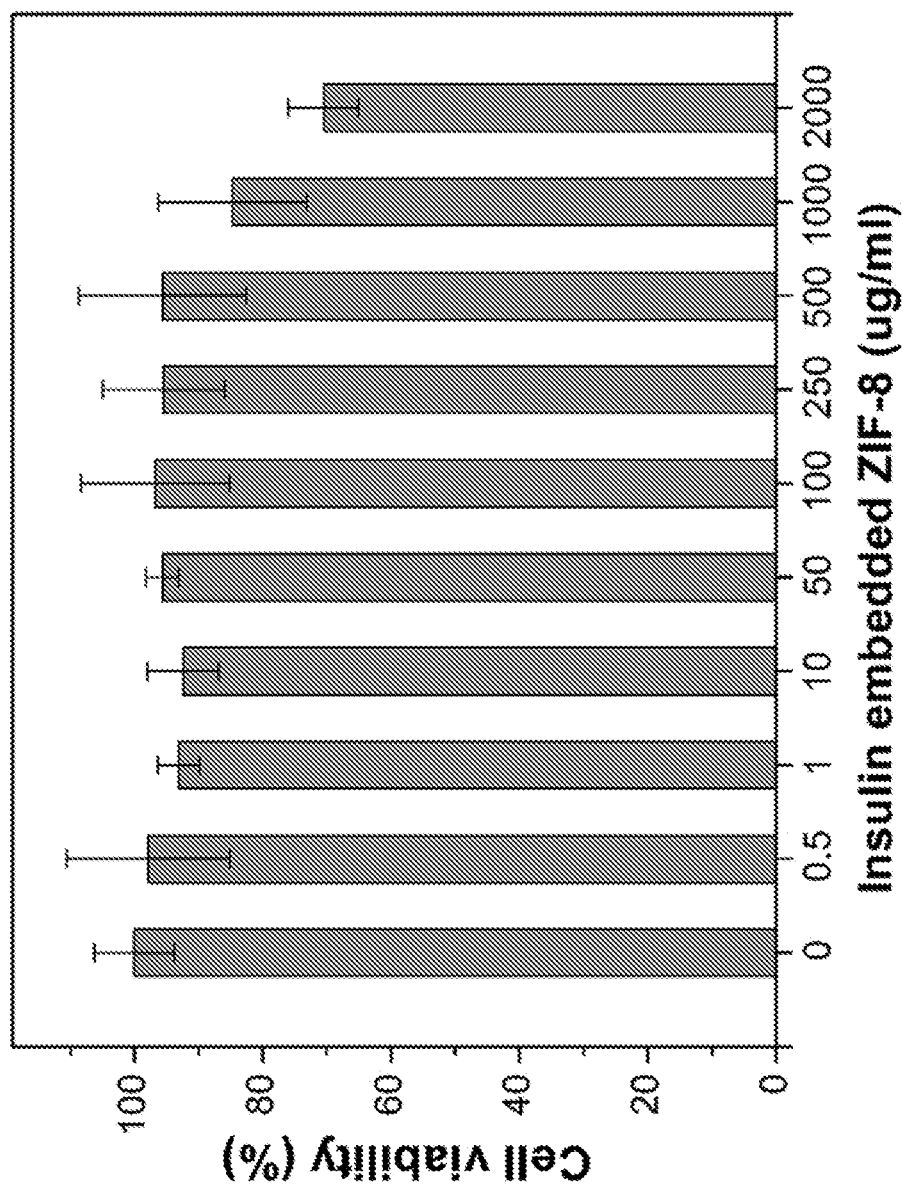
FIG. 33 depicts an exemplary embodiment of cell viability of mouse embryonic fibroblast (cell line: 3T3) exposed to dissociated insulin-embedded ZIF-8 crystals in accordance with the present disclosure.

The biocompatibility of insulin-embedded ZIF-8 (after fully dissociated by EDTA) was assessed by determining its cytotoxicity using MTT assay (FIG. 33 Incubation time: 24 hours. Results are the mean and standard deviation from three independent samples). The mouse embryonic fibroblast 3T3 cells were used as the model cell line. After 24 h incubation with relatively high concentration (1000 μg/mL) of dissociated crystals, the cell viability was found to be higher than 80%, indicating the low cytotoxicity of the dissociated products. To further evaluate the biocompatibility of insulin-embedded ZIF-8, the mice treated with ZIF-8 encapsulated insulin and PBS were sacrificed 5 days after insulin administration for histological analysis. The haematoxylin and eosin (H&E) stained images of various organs from the two groups showed similar structure (FIG. 32B). There were no apparent histopathological abnormalities or lesions observed in the heart, liver, spleen, lung and kidney. In addition, there was no weight loss in either group after 5 days administration (Table 3).

TABLE 3

Mice weight before and 5 days after injection. Results are the mean ± standard deviation (n = 3).

| Group | Before (g) | After (g) |
|---|---|---|
| PBS | 22.5 ± 0.4 | 23.0 ± 1.0 |
| ZIF-8 preserved insulin | 22.7 ± 1.3 | 22.7 ± 1.1 |
| Insulin alone at 40° C. | 22.0 ± 0.2 | 22.5 ± 0.7 |
| Insulin at −20° C. | 23.0 ± 1.4 | 23.2 ± 1.3 |

Figure 34:
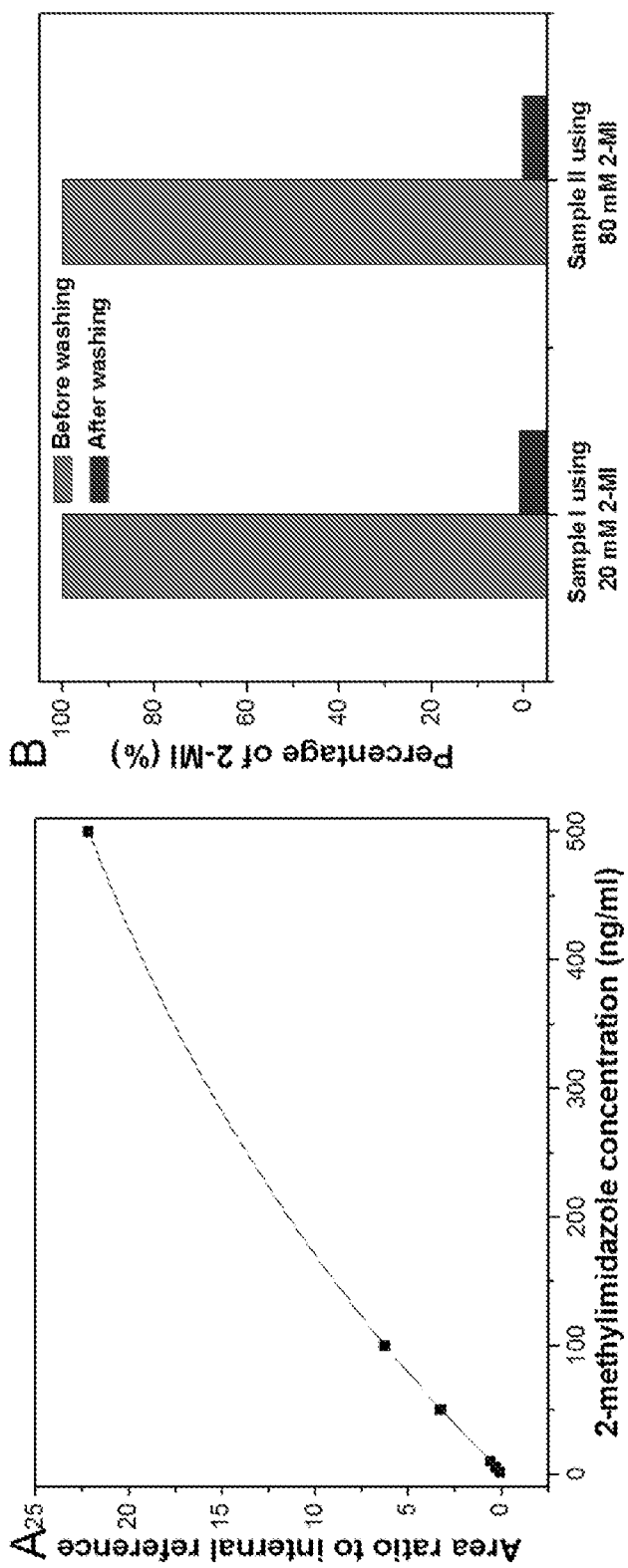
FIG. 34A depicts an exemplary embodiment of a standard curve of 2-methylimidazole plotted by HPLC-mass spectrometry in accordance with the present disclosure.
FIG. 34B depicts an exemplary embodiment of HPLC-mass spectrometry quantification showing a purification step removing over 99% of 2-methylimidazole residues within the solutions of insulin released from ZIF-8 encapsulation in accordance with the present disclosure.

Overall, the insulin-embedded ZIF-8 after dissociation shows excellent biocompatibility. feasibility of removing dissolved ZIF-8 residues before insulin administration was also tested. The ZIF-8 encapsulated insulin was first released by adding EDTA and then filtered to remove any ZIF-8 byproduct using centrifuge tube with 3 kDa filter. After three times washing, HPLC-mass spectrometry analysis showed that more than 99% of 2-methylimidazole is removed (FIG. 34A and FIG. 34B). Sample I and II were made by 20 mM and 80 mM 2-methylimidazole precursor, respectively. This purification step mitigates the toxicity concern from ZIF-8 residue, especially for repeated drug administration as is the case with insulin.

3T3 cell line was harvested with trypsin and resuspended in Dulbecco's modified eagle medium at a concentration of 5×10$^4$ cells per ml. 100 μL per well of the cell suspension was transferred into 96-well plates to preculture for 24 hours. The medium was replaced by a fresh medium that contained different concentrations of dissociated insulin-embedded ZIF-8 crystals. After 24 hours incubation, the medium was removed and cells were washed by DPBS. 100 μL of 1.2 mM MTT medium solution was then added to each well. After 4 hours, the MTT medium was removed and 200 μL DMSO was added to each well. After incubation for 10 min, the absorbance at 570 nm was determined with a plate reader.

Example 12: Methods

Chemicals. 2-methylimidazole, zinc acetate dihydrate, ethylenediaminetetraacetic acid (EDTA), Tween 20, sodium phosphate monobasic, sodium phosphate dibasic, ethyl acetate, (3-(4,5-dimethylthiazol-2-yl)-2,5-diphenyl tetrazolium bromide) (MTT), dimethyl sulfoxide (DMSO) and phosphate-buffered saline (PBS) were purchased from Sigma-Aldrich. Artificial urine (Surine™ Negative Urine Control) was purchased from Cerilliant Company (a Sigma-Aldrich Company). This artificial urine is suitable for LC/MS or GC/MS applications in clinical chemistry, urine drug testing or forensic analysis. No protein and preservatives are added. Human recombinant neutrophil gelatinase-associated lipocalin (NGAL), human recombinant CA-125, NGAL ELISA kit (DY1757, detection range: 78 pg/ml to 5000 pg/ml), and CA-125 ELISA kit (DY5609, detection range: 31.2 pg/ml to 2000 pg/ml) were purchased from R&D systems. Human recombinant insulin and insulin sandwich ELISA kit (detection range, 15.60-1,000 pmol/L) were purchased from R&D systems. Custom protein microarray kits were purchased from RayBiotech (Custom G-Series Antibody Array, AAX-CUST-G). Pierce bicinchoninic acid (BCA) protein assay kit and trypsin were obtained from Thermo Fisher Scientific. For patient samples, approval was obtained from the Washington University Institutional Review Board, and written informed consent was obtained from all patients. Dulbecco's modified eagle medium and Dulbecco's phosphate-buffered saline (DPBS) were purchased from Gibco. All experiments were performed using nanopure water with a resistivity of 18.2 MΩ·cm.

Sample preparation. NGAL-spiked artificial urine (50 μg/ml of NGAL, 25 μl) or patient urine (25 μl) was first mixed with 2-methylimidazole aqueous solution (12.5 μl) and then zinc acetate dihydrate aqueous solution (12.5 μl). The final concentrations of 2-methylimidazole after mixing were 320 mM, 160 mM, 80 mM and 40 mM. The final concentrations of zinc acetate dihydrate after mixing were 80 mM, 40 mM, 20 mM and 10 mM. Note that the molar ratio of 2-methylimidazole to zinc acetate dihydrate were kept at 4:1. Depending on the embodiment, the molar ratio of 2-methylimidazole to zinc acetate dihydrate is in a range of from about 4:1 to about 40:1. For example, in some embodiments, the molar ratio of 2-methylimidazole to zinc acetate dihydrate is about 4:1, about 8:1, about 16:1, about 20:1, or about 40:1. After 1 hour incubation at room temperature (20-23° C.), 50 μl mixture was transferred onto a 2×0.5 cm Whatman 903 paper strip (Sigma) to allow air-drying (usually about 2 hours at room temperature). For accurately determining the NGAL recovery after storage, it is important to avoid liquid leakage from the paper strip during the drop-cast process. Typically, a 2×0.5 cm paper strip is able to absorb 50 μl biofluid without leakage. After drying, the paper strips were sealed in petri dishes and stored at 25° C., 40° C. or 60° C. for different time intervals. The sample preparation for serum and plasma were similar to urine except that the serum and plasma were first diluted 5, 10 or 20 times with PBS and then spiked with CA-125 (50 μg/ml of CA-125). For the fresh blood samples, the CA-125 was first spiked into the blood and then the plasma was separated from the blood using hand-powered centrifuge for the subsequent sample preparation.

Synthesis of insulin-embedded ZIF-8. To form insulin-embedded ZIF-8, 2-methylimidazole solution (0.5 mL, in nanopure water) and zinc acetate dihydrate solution (0.5 mL, in nanopore water) were added into 5 mL of insulin solution (0.6 mg/mL in PBS). The final concentrations of 2-methyl-imidazole after mixing were 40 mM, 80 mM, and 120 mM. The final concentrations of zinc acetate dihydrate after mixing were 10 mM, 20 mM and 30 mM. The molar ratio of 2-methylimidazole and zinc acetate was controlled to be 4:1. Depending on the embodiment, the molar ratio of 2-methylimidazole to zinc acetate dihydrate is in a range of from about 4:1 to about 40:1. For example, in some embodiments, the molar ratio of 2-methylimidazole to zinc acetate dihydrate is about 4:1, about 8:1, about 16:1, about 20:1, or about 40:1. The resultant mixture was incubated at room temperature for 12 h to form insulin-embedded ZIF-8 crystals. For subsequent characterization, the insulin-embedded ZIF-8 crystals were collected by centrifugation (at 13.4 k rpm for 20 min), washed twice by nanopure water and vacuum dried at room temperature. Pure ZIF-8 was synthesized via the similar approach without adding insulin.

Protein recovery. Before analysis, the paper strips were eluted in 1 ml elution buffer (0.2 M phosphate buffer with 2 mM EDTA and 0.1% Tween 20 at pH=5.6) by shaking the paper strip in a cuvette with the elution buffer at the speed of 60 r.p.m. for 1 hour. Different elution buffer recipes were tested for maximal recovery (FIGS. A-S5 and A-S6). The elution solution was then assayed by ELISA for the target analyte. NGAL and CA-125 standards provided with the ELISA kits were used to generate a standard curve for each assay.

Characterization. To characterize protein-embedded crystals, crystals were centrifuged and washed with DI water twice (8 k r.p.m. for 20 minutes). To calculate the encapsulation efficiency, the supernatant after first centrifugation was collected and assayed by ELISA. SEM images were obtained using a FEI Nova 2300 field-emission scanning electron microscope at an acceleration voltage of 10 kV. Fourier transform infrared spectroscopy (FTIR) measurements were conducted using a Nicolette Nexus 470 spectrometer. The Raman spectra were obtained using a Renishaw inVia confocal Raman spectrometer mounted on a Leica microscope with a 50× objective and a 514 nm wavelength diode laser as an illumination source. The X-ray diffraction (XRD) measurements of the samples were recorded on a Bruker D8-Advance X-ray powder diffractometer using Cu Kα radiation ($\lambda$=1.5406 Å).

Characterization of insulin-embedded ZIF-8. Scanning electron microscopy (SEM) images were obtained using a FEI Nova 2300 field-emission SEM at an acceleration voltage of 10 kV. Transmission electron microscopy (TEM) micrographs were collected by a JEM-2100F (JEOL) field emission instrument. Thermogravimetric analysis (TGA) was performed using TA Instruments Q5000 IR Thermogravimetric Analyzer in air (at rate of 5° C. min-1). Fourier transform infrared spectroscopy (FTIR) measurements were performed using a Nicolette Nexus 470 spectrometer. The Raman spectra were obtained using a Renishaw inVia confocal Raman spectrometer mounted on a Leica microscope with a 50× objective and a 514 nm wavelength diode laser as an illumination source. The X-ray diffraction (XRD) measurements of the samples were recorded on a Bruker D8-Advance X-ray powder diffractometer using Cu Kα radiation ($\lambda$=1.5406 Å) with scattering angles (28) of 5-35°.

Evaluation of preservation efficacy under environmental stressors using ELISA. To evaluate the preservation efficacy under non-refrigerated temperatures, the vials with suspension of insulin embedded ZIF-8, pure insulin or insulin with adding zinc acetate solutions were sealed and stored at 25, 40 and 60° C. for different time intervals (including 1, 2, 3 and 4 weeks). Insulin sandwich ELSIA was used to quantify the insulin recovery after storage. Before ELISA measurement, the ZIF-8 encapsulated insulin was released by adding EDTA (with same molar amount as zinc acetate). The preservation efficacy was calculated by comparing the recovered insulin amount to day 0 insulin amount prior to heating. To examine the preservation efficacy under agitation, insulin in PBS (0.5 mg/mL, 1 mL) with and without ZIF-8 encapsulation was vortexed at 200 rpm for 48 h. To assess the preservation efficacy under organic solvent, insulin in PBS (0.5 mg/mL, 1 mL) with and without ZIF-8 encapsulation was first mixed with ethyl acetate (1 mL), and then shaken for 6 h. The ethyl acetate was removed by vacuum drying before ELISA measurement.

Circular dichroism (CD) spectroscopy. The CD measurements were performed using a spectropolarimeter JASCO J-810. The spectrum was collected at the rate of 20 nm per minute at a response time of 16 seconds. Before CD measurement, the ZIF-8 encapsulated insulin was first released by adding EDTA and then filtered to remove any ZIF-8 byproduct using centrifuge tube with 3 kDa filter. The insulin recovered from various treatments was quantified by BCA assay and diluted to 100 μg/mL in PBS. The secondary structures of insulin ($\alpha$-helical content, $\beta$-sheet content) were analyzed using CDPro software from CD spectra.

High-performance liquid chromatography (HPLC). Insulin was analyzed using a method based on the United States Pharmacopeia Insulin Monograph (http://www.pharmacopeia.cn/v29240/usp29nf24s0_m40520.html) and Waters Application Note Final Transferred UPLC Method (http://www.waters.com/webassets/cms/library/docs/720001396en.pdf) with minor modification. Before HPLC measurement, the ZIF-8 encapsulated insulin was first released by adding EDTA and then filtered to remove any ZIF-8 byproduct using centrifuge tube with 3 kDa filter. HPLC-UV was conducted on an Agilent (Santa Clara, CA) HPLC 1100 series system composed of a binary pump with a micro vacuum degasser, thermostatted column oven, high performance micro well plate autosampler, and variable wavelength detector. ChemStation B.04.03 software was utilized for instrument control, data acquisition, peak integration and data analysis. Chromatographic separation was achieved utilizing a Kinetex Core-Shell analytical column (100×2.1 mm, 2.6 μm, Phenomenex, Torrance, CA). A 0.25 μM inline filter was additionally added prior to the sample entering the column. The injection volume was 5 μL.

HPLC-mass spectrometry analysis of 2-methylimidazole residues before and after purification. HPLC-mass spectrometry analysis was performed on an ultra-fast liquid chromatography system (Shimadzu Scientific Instruments, Columbia, MD) with a CMB-20A system controller, two LC-20AD XR pumps, DGU-20A3 degasser, SIL-20AC XR autosampler, FCV-11AL solvent selection module, and CTO-20A column oven, and an external Valco divert valve installed between the LC and mass spectrometer. The LC system was coupled to an API 4000 linear ion trap triple quadrupole (QTRAP) tandem mass spectrometer operated with Analyst 1.5.2. Multiquant 3.0.1 (AB Sciex) was utilized for peak integration, generation of calibration curves, and data analysis. Chromatographic separation was achieved with a Sunfire C18 (150×2.1 mm, 3.5 μM, Waters, Milford, MA) analytical column equipped with a C18 VanGuard cartridge (2.1 mm×5 mm, 3.5 μM, Waters, Milford, MA). A 0.25 μM inline filter was additionally added prior to the sample entering the column. The flow rate was 0.4 mL/min with a mobile phase consisting of 20 mM ammonium formate aqueous (A) and 20 mM ammonium formate in methanol (B). The column was equilibrated with 0% B, maintained after injection for 1.0 min, then a linear gradient to 80% B applied over 1.25 minutes and held for 2.75 min, then reverted back to 0% B over 0.1 min and re-equilibrated for 2.9 min. Total run time was 8 min. The injection volume was 10 µl. The column oven was at 40° C. Under these conditions, approximate retention time for 2-methylimidazole was 1.77 minutes and for 4-methylimidazole (internal reference) was 3.18 minutes. The mass spectrometer electrospray ion source was operated in positive ion multiple reaction monitoring mode. The [M+H]+ transitions were optimized for 2-methylimidazole 83.0→42.2 and 4-methylimidazole 83.0→56.2. Mass spectrometer settings for the declustering potential (66, 56 V), collision energy (29, 25 V), entrance potential (10 V), and collision cell exit potential (4, 8 V) were optimized. Optimized global parameters were: source temperature 550° C., ionspray voltage 5000 V, nitrogen (psig) curtain gas 30, gas 1 50, gas 2 50, collision gas medium. Similar as CD experiments, the ZIF-8 encapsulated insulin was first released by adding EDTA and then filtered to remove any ZIF-8 byproduct using centrifuge tube with 3 kDa filter (three times washing with water and using 3000 rpm for 5 minutes at each time). HPLC-mass spectrometry was used to quantify the 2-methylimidazole before and after washing.

SDS-PAGE and Western blotting protocols. For SDS-PAGE, 300 µl of eluate was mixed with 0.9 ml acetone-methanol (1:1), placed on ice for 1 hour and centrifuged at 10,000 r.p.m. for 10 minutes to precipitate and concentrate the eluted urine or serum proteins. The protein pellet was briefly air dried and re-suspended in SDS sample buffer containing 5% mercaptoethanol. A 5 µl sample was applied to each well of a NuPAGE 4-12% acrylamide Bis-Tris gel (Invitrogen, San Diego, CA). The proteins were separated at a constant 200 volts for 35 minutes using MES running buffer. The gel was stained with 0.1% coomassie brilliant blue solution for 3 hours and then de-stained overnight.

For western blotting of patient urine samples, 100 µl thawed urine was mixed with 1 ml acetone-methanol (1:1) and placed on ice for 1 hour for precipitation, gathered by centrifugation and re-suspended in SDS sample buffer containing 5% mercaptoethanol. After SDS-PAGE, the urine proteins and pre-stained molecular weight markers were transferred to nitrocellulose membranes for 6 minutes using iBLOT (Invitrogen). The nitrocellulose membrane was briefly washed with water and the non-specific sites blocked with LI-COR block solution (LI-COR Biosciences, Lincoln, NE). Urinary albumin and NGAL were visualized by incubation with 1/2000 dilution of rabbit anti-human serum albumin (Abcam, Cambridge, UK) and 1/500 dilution of goat anti-human NGAL (R&D Systems, Minneapolis, MN) in LI-COR block buffer containing 0.05% Tween-20 (Sigma-Aldrich, St. Louis, MO) overnight. The membrane was then washed three times with phosphate-buffered saline containing 0.05% Tween-20 followed by incubation with 1/10,000 dilutions each of Donkey anti-rabbit IgG 680 and Donkey anti-goat IgG 800 (LI-COR Biosciences). After 1 hour, the membrane was washed four times with phosphate-buffered saline containing 0.05% Tween-20 and visualized using an Odyssey-Fc (LI-COR Biosciences).

Protein microarray protocols. Commercial protein microarray chip was purchased from RayBiotech (Custom G-Series Antibody Array, AAX-CUST-G). Antibodies were printed on a glass slide with 4 subarrays available per slide. The slide was blocked by 1× blocking buffer (0103004-B) for 30 minutes. The eluted urine samples were added into each sub-well of the microarray chip for 2 hours incubation at room temperature. The chip was then washed thoroughly with 1× wash buffers (0103004). 70 µl of 1× biotin-conjugated anti-cytokines were added to each subarray and the chip was incubated in room temperature with gentle shaking. After 2 hours, the chip was washed and 70 µl of streptavidin-CW800 (100 ng/ml in 1× blocking buffer) was added and incubated in dark for 20 mins. The chip was washed thoroughly with wash buffer then nanopure water and blow dried under nitrogen gas. The glass chip was scanned by Licor Odyssey CLx scanner using 800 nm channel (intensity=2, resolution=21 µm, scanning height=1 mm). Median background signal was adopted for analysis spot intensity.

CD spectroscopy. The CD measurements were performed using a spectropolarimeter JASCO J-810. The spectrum was collected at the rate of 20 nm per minute at a response time of 16 seconds. Before CD measurement, the ZIF-8 encapsulated HSA was first eluted and then filtered to remove any ZIF-8 byproduct using centrifuge tube with 30 kDa filter. The HSA recovered from various treatments was quantified by BCA assay for calculating molar ellipticity. The secondary structures of HSA ($\alpha$-helical content, $\beta$-sheet content) were analyzed using CDPro software from CD spectra.

Paperfuge. The paperfuge was composed of a paper disc, a string and glass capillaries (microhematocrit capillary tubes, D=1.55 mm, Fisher Scientific). Common wood was used for the handles. The string was immobilized through paper disc using epoxy. After drawing blood, one end of capillary was sealed by capillary tube sealing tray (Thomas Scientific).

It is to be understood that the configurations and/or approaches described herein are exemplary in nature, and that these specific aspects or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and sub-combinations of the various processes, systems and configurations, and other features, functions, acts, and/or properties disclosed herein, as well as any and all equivalents thereof.

What is claimed is:
1. A method of preparing a biological sample comprising:
   contacting a preserving agent with a biological sample to form a mixture, wherein the preserving agent is selected from at least one of a metal-organic framework (MOF) encapsulant or a precursor forming a MOF encapsulant, and wherein the biological sample comprises a biofluid comprising at least one target analyte; and
   drop casting the mixture onto a fibrous substrate;
   wherein the fibrous substrate is made of paper or cellulose; and
   wherein a crystal interface is created between the protein and the fibrous substrate.
2. The method according to claim 1, wherein the MOF is selected from the group consisting of a zeolitic imidazolate framework (ZIF) type MOF and a Materials of Institut Lavoisier (MIL) type MOF.

3. The method according to claim 1, wherein the precursor forming the MOF encapsulant comprises 2-methylimidazole and zinc acetate.

4. The method according to claim 3, wherein a molar ratio of 2-methylimidazole to zinc acetate is in a range of from about 4:1 to about 40:1.

5. The method according to claim 1, wherein the substrate comprises a water insoluble material.

6. The method according to claim 1, further comprising drying the mixture on the substrate.

7. The method according to claim 1, further comprising storing the substrate:
   at a temperature of from about −20° C. to about 100° C.; and
   for at least 1 week, at least 2 weeks, at least 3 weeks, at least 4 weeks, at least 6 months, at least 1 year, or at least 5 years.

8. The method according to claim 1, further comprising recovering the at least one target analyte from the substrate using an elution buffer, wherein the elution buffer has a pH of about 6 or less.

9. The method according to claim 1, wherein the biological sample comprises a biofluid selected from the group consisting of urine, blood, serum, plasma, saliva, and cerebrospinal fluid.

10. The method according to claim 1, wherein the at least one target analyte comprises at least one of a biomarker, a protein biomarker, a protein therapeutic, an antibody, a viral protein, an oligonucleotide, DNA, RNA, a macromolecule having a primary structure and a secondary structure, a protein having an amino acid sequence from an organism, and a polypeptide having an amino acid sequence from an organism;
   wherein the protein biomarker is selected from the group consisting of neutrophil gelatinase-associated lipocalin (NGAL), kidney injury molecule-1 (KIM-1), albumin, beta-2 microglobulin, cystatin C, cancer antigen 125 (CA-125), prostate-specific antigen (PSA), human IgG and IgM, ZIKV nonstructural protein 1, and cytokines; and
   wherein the protein therapeutic is selected from the group consisting of insulin, monoclonal antibodies, erythropoietin, cytokines, and vaccines.

\* \* \* \* \*